United States Patent
De Weer et al.

(10) Patent No.: US 10,493,158 B2
(45) Date of Patent: *Dec. 3, 2019

(54) PHARMACEUTICAL COMPOSITIONS FOR THE TREATMENT OF INFLAMMATORY DISORDERS

(71) Applicant: GALAPAGOS NV, Mechelen (BE)

(72) Inventors: Marc Maurice Germain De Weer, Mechelen (BE); Sara Bertha Camiel Vrielynck, Mechelen (BE); Nicolas Luc Sabourault, Romainville (FR); Jan Peter Moeschwitzer, Straßberg (DE)

(73) Assignee: GALAPAGOS NV, Mechelen (BE)

( * ) Notice: Subject to any disclaimer, the term of this patent is extended or adjusted under 35 U.S.C. 154(b) by 160 days.

This patent is subject to a terminal disclaimer.

(21) Appl. No.: 14/614,393

(22) Filed: Feb. 4, 2015

(65) Prior Publication Data
US 2015/0224199 A1    Aug. 13, 2015

(30) Foreign Application Priority Data

Feb. 7, 2014    (GB) .................................. 1402070.5

(51) Int. Cl.
| A61K 47/32 | (2006.01) |
| --- | --- |
| A61K 45/06 | (2006.01) |
| A61K 47/02 | (2006.01) |
| A61K 47/44 | (2017.01) |
| A61K 31/541 | (2006.01) |
| A61K 47/38 | (2006.01) |
| A61K 9/20 | (2006.01) |
| A61K 9/48 | (2006.01) |

(52) U.S. Cl.
CPC ............ *A61K 47/32* (2013.01); *A61K 9/2054* (2013.01); *A61K 9/4866* (2013.01); *A61K 31/541* (2013.01); *A61K 45/06* (2013.01); *A61K 47/02* (2013.01); *A61K 47/38* (2013.01); *A61K 47/44* (2013.01)

(58) Field of Classification Search
None
See application file for complete search history.

(56) References Cited

U.S. PATENT DOCUMENTS

| 6,500,854 | B1 | 12/2002 | Kitamura et al. | |
| --- | --- | --- | --- | --- |
| 8,088,764 | B2 * | 1/2012 | Menet .................. | C07D 471/04 514/228.5 |
| 8,242,274 | B2 | 8/2012 | Menet et al. | |
| 8,563,545 | B2 * | 10/2013 | Menet .................. | C07D 471/04 514/228.5 |
| 8,999,979 | B2 * | 4/2015 | Menet .................. | C07D 471/04 514/228.5 |
| 9,309,244 | B2 * | 4/2016 | Menet .................. | C07D 471/04 |
| 9,382,247 | B2 * | 7/2016 | Sabourault .......... | A61K 31/437 |
| 9,415,037 | B2 * | 8/2016 | Menet .................. | C07D 471/04 |
| 9,707,237 | B2 * | 7/2017 | Menet .................. | C07D 471/04 |
| 2005/0222171 | A1 | 10/2005 | Bold et al. | |
| 2008/0274178 | A1 * | 11/2008 | Imamoto .............. | A61K 9/0056 424/465 |
| 2010/0029709 | A1 * | 2/2010 | Menet .................. | C07D 471/04 514/303 |
| 2013/0310340 | A1 | 11/2013 | Payan et al. | |
| 2014/0271842 | A1 * | 9/2014 | Herbig ................. | A61K 31/519 424/457 |

FOREIGN PATENT DOCUMENTS

| EP | 1 391 211 | 2/2004 |
| --- | --- | --- |
| WO | 2003010167 | 2/2003 |

(Continued)

OTHER PUBLICATIONS

Cancer Drug Design and Discovery Neidle, Stephen, ed. (Elsevier/Academic Press, 2008) pp. 427-431.*
Kopf et al., Averting inflammation by targeting the cytokine environment Nature Reviews, Drug Discovery, vol. 9, Sep. 2010, 703-718.
Mullighan, et al., JAK mutations in high-risk childhood acute lymphoblastic leukemia, PNAS, 2009, 106(23), 9414-18.
O'Sullivan et al., Cytokine receptor signaling through the Jak-Stat-Socs pathway in disease, Molecular Immunology 44 (2007) 2497-2506.

(Continued)

*Primary Examiner* — Jeffrey S Lundgren
*Assistant Examiner* — William Y Lee
(74) *Attorney, Agent, or Firm* — Arent Fox LLP

(57) ABSTRACT

The present invention discloses pharmaceutical compositions comprising: a compound according to Formula I:

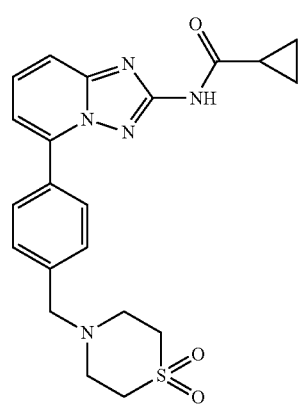

useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

18 Claims, 15 Drawing Sheets

(56) References Cited

FOREIGN PATENT DOCUMENTS

| WO | 2004072072 | 8/2004 |
| WO | 2005124342 | 12/2005 |
| WO | 2006018735 | 2/2006 |
| WO | 2006038116 | 4/2006 |
| WO | 2007009773 | 1/2007 |
| WO | 2008025821 | 3/2008 |
| WO | 2008150015 | 11/2008 |
| WO | 2009010530 | 1/2009 |
| WO | 2009017954 | 2/2009 |
| WO | 2009027283 | 3/2009 |
| WO | 2009047514 | 4/2009 |
| WO | 2009155565 | 12/2009 |
| WO | 2010010184 | 1/2010 |
| WO | 2010010186 | 1/2010 |
| WO | 2010010187 | 1/2010 |
| WO | 2010010188 | 1/2010 |
| WO | 2010010189 | 1/2010 |
| WO | 2010010190 | 1/2010 |
| WO | 2010010191 | 1/2010 |
| WO | 2010141796 | 12/2010 |
| WO | 2010149771 | 12/2010 |
| WO | W02010149769 | 12/2010 |
| WO | WO 2013/189771 | 12/2013 |

OTHER PUBLICATIONS

Vainchenker et al., JAKs in pathology: Role of Janus kinases in hematopoietic malignancies and immunodeficiencies, Seminars in Cell & Developmental Biology, 2008, 19, 385-393.

Xiang et al., Identification of somatic JAK1 mutations in patients with acute myeloid leukemia, Blood, 2008, 111: 4809-4812.

Zikherman et al., Unraveling the functional implications of GWAS: how T cell protein tyrosine phosphatase drives autoimmune disease, J Clin Invest., 2011, 121(12), 4618-4621.

Zenz et al., Psoriasis-like skin disease and arthritis caused by inducible epidermal deletion of Jun proteins, Nature, 2005, 437, 369-375.

Dolgin, Elie, Companies hope for kinase inhibitor JAKpot, Nature Reviews Drug Discovery, Oct. 2011, 10, 717-718.

Punwani et al., Preliminary clinical activity of a topical JAK1/2 inhibitor in the treatment of psoriasis, J Am Acad Dermatol, 2012, 67(4), 658-64.

Ingersoll et al., The impact of medication regimen factors on adherence to chronic treatment: a review of literature, J Behav Med., Jun. 2008, 31(3), 213-224.

Verstovsek S, Therapeutic potential of JAK2 inhibitors, Hematology Am Soc Hematol Educ Program, 2009, 636-42.

Zhang et al., Activation of Jak/STAT proteins involved in signal transduction pathway mediated by receptor for interleukin 2 in malignant T lymphocytes derived from cutaneous anaplastic large T-cell lymphoma and Sezary syndrome, Proc. Natl. Acad. Sci. USA, Aug. 1996, vol. 93, pp. 9148-9153.

Berishaj et al., Stat3 is tyrosine-phosphorylated through the interleukin-6/glycoprotein 130/Janus kinase pathway in breast cancer, Breast Cancer Res. 2007, 9(3), R32.

O'Dell, Therapeutic Strategies for Rheumatoid Arthritis;2004 N Eng J Med, 350, 2591-602.

Naka T et al., the paradigm of IL-6: from basic science to medicine. Arthritis Res,2002; 4 (suppl 3), S233-S242.

Yu Lx et al, Influence of drug release properties of conventional solid dosage forms on the systemic exposure of highly soluble drugs. AAPS pharmsci, 2001; 3(3), E24.

CHMP, Guideline on Clinical Investigation of Medicinal Products indicated for the treatment of Psoriasis., 2004.

Lipinski et al., Experimental and computational approaches to estimate solubility and permeability in drug discovery and development settings, Advanced Drug Discovery Reviews, 46: 3-26, (2001).

Smolen J.S. et al, Therapeutic strategies for rheumatoid arthritis, Nat Rev Drug Discov, 2003, 2(6), 473-88.

Tam et al., Expression levels of the JAK/STAT pathway in the transition from hormone-sensitive to hormone-refractory prostate cancer, British Journal of Cancer, 2007, vol. 97, 378-383.

Constantinescu et al., Mining for JAK-STAT mutations in cancer, Trends in Biochemical Sciences, vol. 33, No. 3, 122-131.

Softfocus SKF Directed Libraries; Library SFK 39, "Serine-Threonine and Tyrosine Kinase directed", BioFocus DPI, Advertising Article, 2006.

Bain, J., et al.—Biochem. J. (2003) 371: 199-204—"The specificities of protein kinase inhibitors: an update,".

Levy, et al.—N Engl J Med (2007) 357: 1655-1658—"STAT3 Signaling and the Hyper-IgE Syndrome".

McGinnity, et al.—Drug Metab Disp., (2004) 32(11): 1247-1253—"Evaluation of fresh and cryopreserved hepatocytes as in vitro drug metabolism tools for the prediction of metabolic clearance".

Fabian, et al.—Nature Biotech., (2005) 23(3): 329-336—"A small molecule-kinase interaction map for clinical kinase inhibitors".

Vainchenker, et al.—Pathol Biol., 55 (2007) 88-91—"JAK2, the JAK2 V617F mutant and cytokine receptors".

Choy, et al.—N Engl J Med., 344 (2001) 907-16—"Cytokine Pathways and Joint Inflammation in Rheumatoid Arthritis".

Chubinskaya, et al.—The Int'l Journal of Biochem. & Cell Bio., 35 (2003) 1323-1340—"Regulation of osteogenic proteins by chondrocytes".

Clegg, et al.—N Engl J Med., (2006) 354 (8) 795-808—Glucosamine, Chondroitin Sulfate, and the Two in combination for Painful Knee Osteoarthritis.

Firestein, G S—Nature 423 (2003) 356-61—"Evolving concepts of rheumatoid arthritis".

Kachigian, L M—Nature Protocols (2006) 1 (5) 2512-2516—"Collagen antibody-induced arthritis".

Lee, et al.—Lancet (2001) 358: 903-11—"Rheumatoid Arthritis".

Legendre, et al.—J. Biol Chem. (2003) 278(5) 2903-2912—"JAK/STAT but not ERK1/ERK2 pathway mediates interleuking . . .".

Osaki, et al.—Biochem J. (2003) 369: 103-115—"The TATA-containing core promoter of the type II collagen gene . . .".

Li, et al.—The J. of Immuno. (2001) 166: 3491-3498—"Oncostatin M-induced matrix metalloproteinase and tissue inhibitor of . . .".

Oste, et al.—ECTC Montreal 2007—"A high throughput method of measuring bone architectural disturbance in a murine CIA model by micro-CT morphometry".

Otero, et al.—Arthritis Research & Therapy (2005) 7(3) 581-591—"Signalling pathway involved in nitric oxide synthase type II . . .".

Rodig, et al.—Cell (1998) 93: 373-383—"Disruption of the Jak1 gene demonstrates".

Sims, et al.—Arthritis & Rheumatism (2004) 50(7) 2338-2346—"Targeting Osteoclasts with Zoledronic Acid prevents Bone Destruction in Collagen-Induced Arthritis".

Wernig, et al.—Cancer Cell (2008) 13(4) 311-320—"Efficacy of TG101348, a selective JAK2 inhibitor, in treatment of a mu rine . . .".

Geron, et al.—Cancer Cell (2008) 13(4) 321-330—"Selective inhibition of JAK2-driven erythroid diffferentiation of polycythemia . . .".

Wieland, et al.—Nat. Rev. Drug Discov. (2005) 4: 331-44—"Osteoarthritis—an untreatable disease".

Wirtz, et al.—Advanced Drug Delivery Reviews (2007) 1073-1083—"Mouse models of inflammatory bowel disease".

Naka, et al.—Arthritis Res (2002) 4 (suppl 3) S233-S242—"The paradigm of IL-6: from basic science to medicine".

O'Shea, et al.—Nature Reviews (2004) 3: 555-564—"A New Modality for Immunosuppression: Targeting the Jak/Stat Pathway".

Nials, et al.—Disease Models & Mechanisms (2008) 213-220—"Mouse Models of Allergic Asthma: Acute and Chronic Allergen Challenge".

Ip, et al.—British Society for Immunology: Clinical and Experimental Immunology (2006) 145: 162-172—Interleukin (IL)-4 and IL-13 up-regulate monocyte chemoattractant protein-1 . . . .

Pernis, et al.—J. Clin. Invest.(2002), 109: 1279-1283—"JAK-STAT signaling in asthma".

(56) References Cited

OTHER PUBLICATIONS

Kudlacz, et al.—Eur. J. Pharmaco 582 (2008) 154-161—"The JAK-3 inhibitor CP-690550 is a potent anti-inflammatory agent in a murine model of pulmonary eosinophilia".
Argiles, et al.—Curr. Opin Clin Nutr Metab Care (1998) 1: 245-251—"Catabolic proinflammatory cytokines".
Bush, et al.—Arthritis Rheum. (2002) 46: 802-5—"Reduction of joint inflammation and bone erosion in rat adjuvant arthritis by treatment with interleukin-17 receptor IgGI Fc fusion protein".
Jou, et al.—Arthritis & Rheum. (2005) 1: 339-344—"Thrombospondin 1 as an effective gene therapeutic strategy in collagen-induced arthritis".
Nishida, et al.—Arthritis & Rheum. (2004) 50: 3365-3376—"Histone Deacetylase Inhibitor Suppression . . .".
Rall, et al.—Rheumatology (2004) 43: 10: 1219-1223—"Rheumatoid cachexia: metabolic abnormalities, mechanisms and interventions".
Salvemini, et al.—Arthritis & Rheum. (2001) 44: 12: 2909-2921—"Amelioration of Joint Disease in a Rat Model of Collagen-induced Arthritis . . .".
Shelton, et al.—Pain. 116 (2005) 8-16—"Nerve growth factor mediates hyperalgesia and cachexia in auto-immune arthritis".
Walsmith, et al.—The Journal of Rheum. (2004) 31: 23-9—"Tumor Necrosis Factor-alpha Production is associated with less body cell mass . . .".
Lin, et al.—The British Journal of Pharma. (2007) 150, 862-872—"Anti-rheumatic activities of histone deacetylase (HDAC) inhibitors in vivo in collagen-induced arthritis in rodents".
Nettekoven, et al.—Synthesis (2003) 11, 1649-1652—"Synthetic Access to 2-Amido . . .".
Laurence, et al.—Open Rheum. Journal (2012) 6 (Suppl 2: M4): 232-244—"JAK Kinases in Health and Disease: An Update".
Changelian, et al.—Blood (2008) 111: 2155-2157—"The specificity of JAK3 kinase inhibitors".
Chen, et al.—Immunity (2012) 36: 529-541—"Janus Kinase Deregulation in Leukemia and Lymphoma".
O'Shea, et al.—Immunity (2008) 28(4): 477-487—"Cytokine signaling modules in inflammatory responses".
O'Shea, et al.—Immunity (2012) 36(4): 542-550—"JAKS and STATs in Immunoregulation and Immune-Mediated Disease".
Van Vollenhoven, et al.—New England Journal of Medicine (2012) 367: 508-519—"Tofacitinib or Adalimumab versus Placebo in Rheumatoid Arthritis".
Saharinen, et al.—Molecular and Cellular Biology (2000) 20 (10): 3387-3395—"Regulation of the Jak2 Tyrosine Kinase by Its Pseudokinase Domain".
Bundgard—Adv. Drug Del Rev. (1992) 8: 1-38—"Prodrugs as a means to improve the delivery of peptide drugs".
Drug Discovery and Development, Understanding the R&D Process—Pharmaceutical Research and Manufacturers of America, 2007; pp. 1-14.
Dymock, J. Develop Drugs, "Recent News in the Fast-Paced Field of JAK Inhibitors", 2013; 2(2): 1-2.
Labadie, et al.—Bioorganic & Medicinal Chemistry Letters (2013) 23: 5923-5930—"Design and evaluation novel 8-0x0-pyridopyrimidine JAK 1/2".
John, et al., "Formulating Weakly Basic HCl Salts: Relative Ability of Common Excipients to Induce Disproportionation and the Unique Deleterious Effects of Magneisum Stearate," Pharmaceutical Research 30(6) • Mar. 2013.

* cited by examiner

Figure 1. [Compound 1.HCl.3H$_2$O] adduct XRPD spectrum.
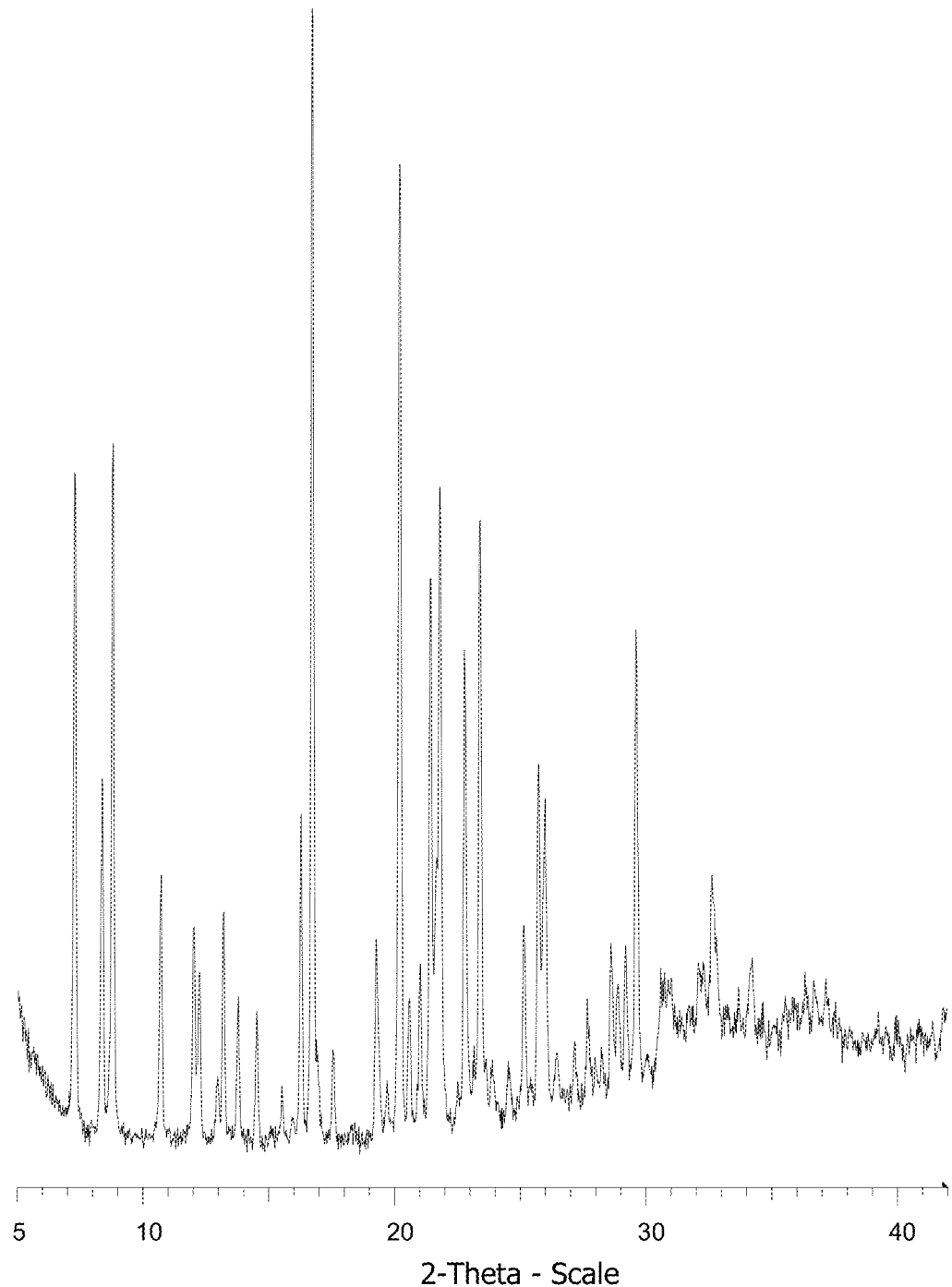

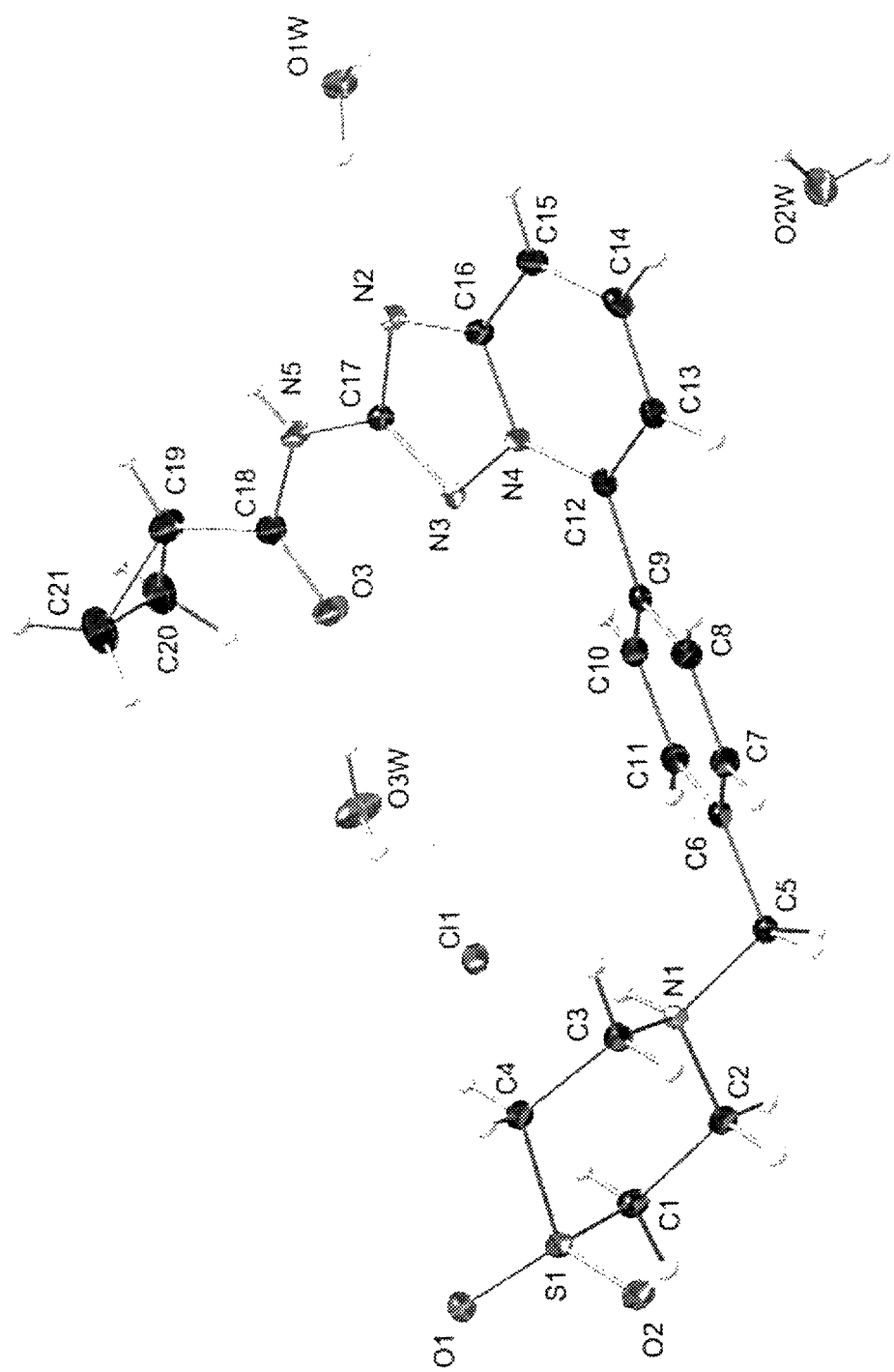
Figure 2. Compound 1.HCl.3H₂O crystal structure

Figure 3. [Compound 1.HCl.3H$_2$O] adduct AUC values following once daily p.o. dosing.
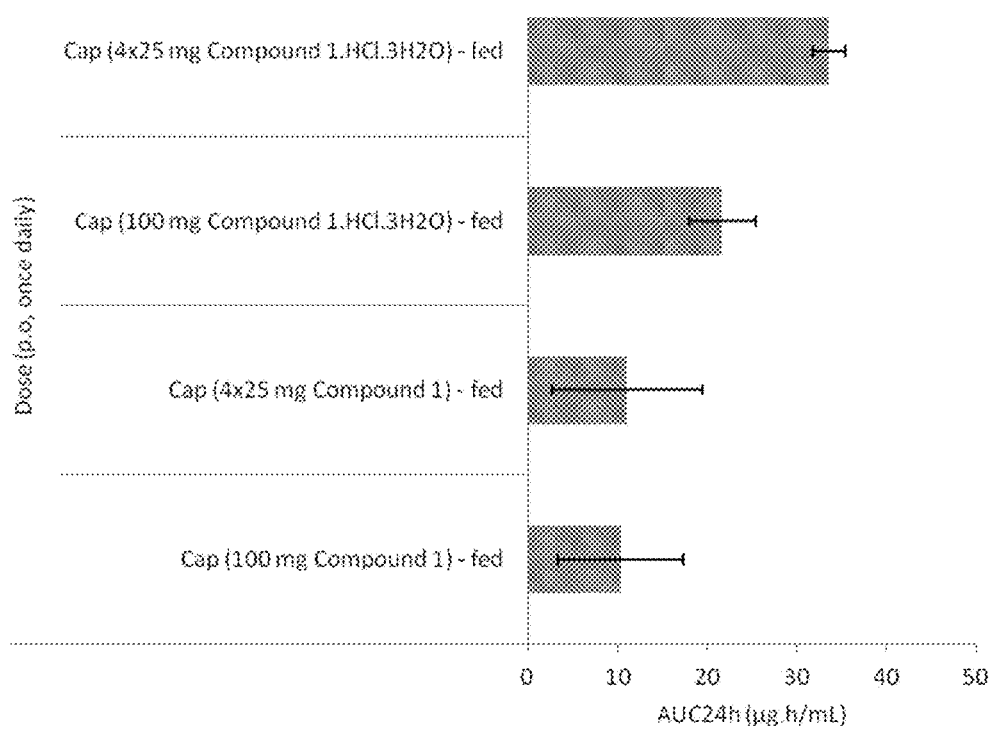

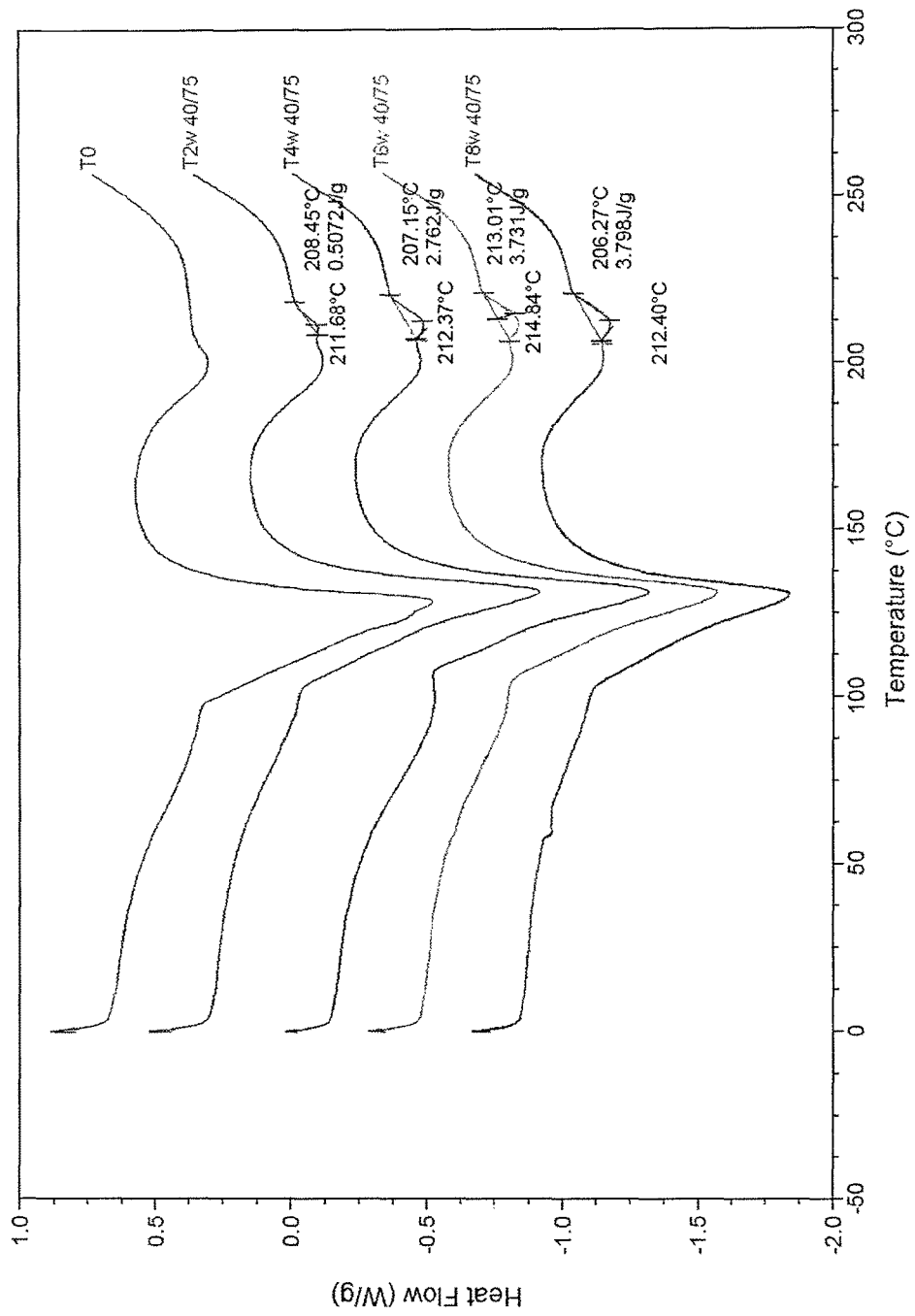
Figure 4. DSC – Capsule A – Accelerated conditions (40°C/75% RH)

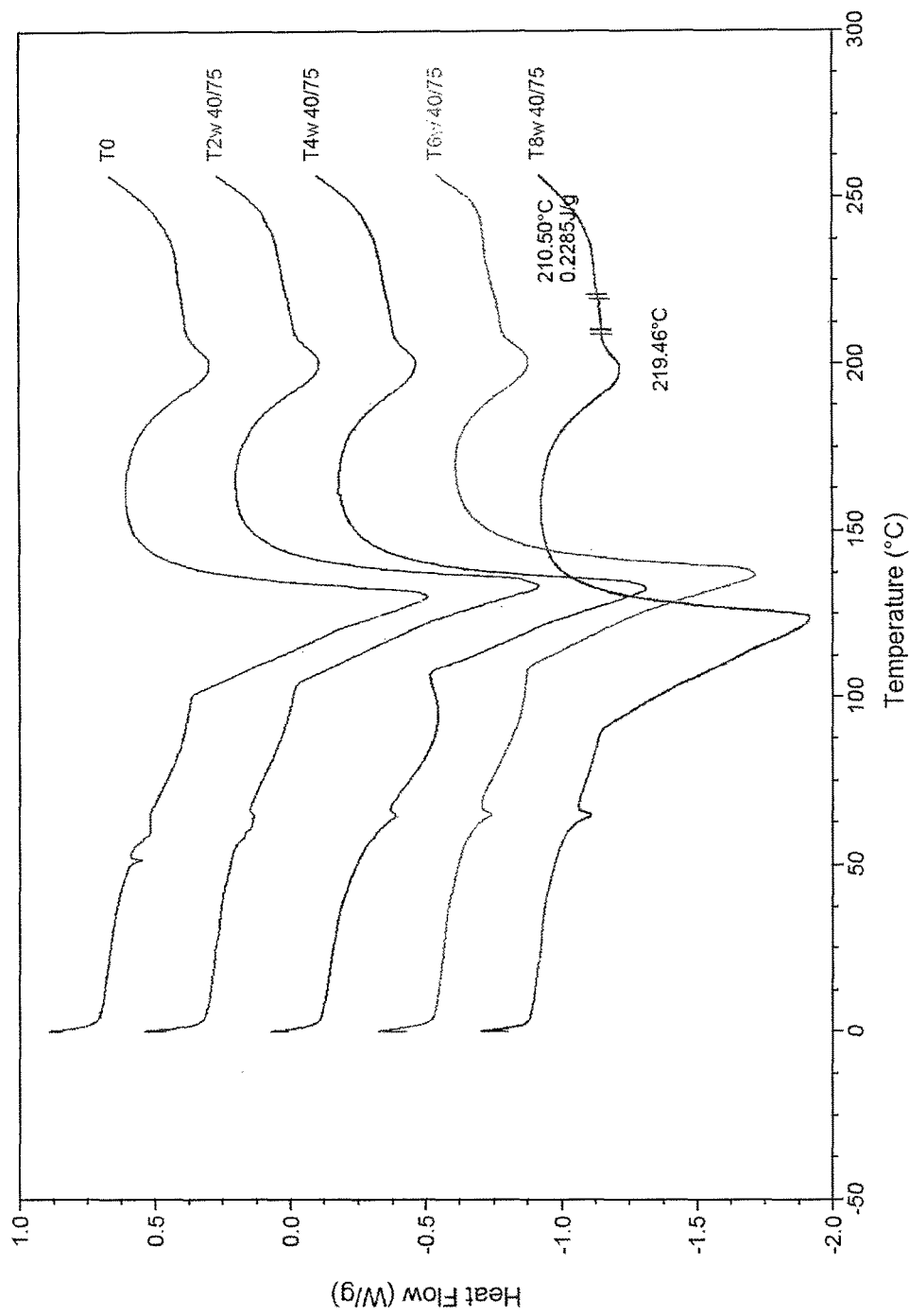
Figure 5. DSC – Capsule B – Accelerated conditions (40°C/75% RH)

Figure 6. Tablet A – Long term storage conditions (25°C/60% RH)
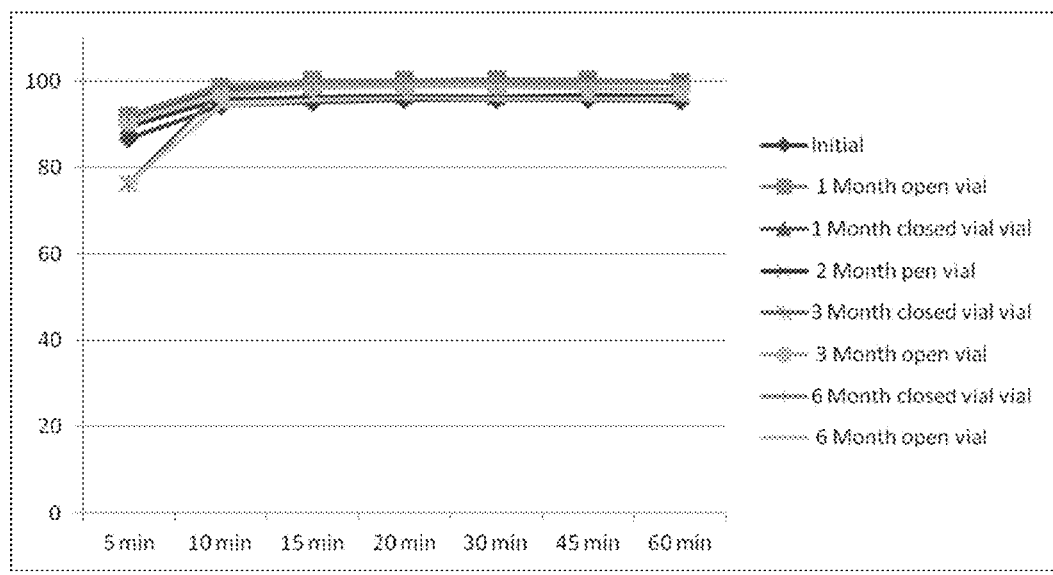
Figure 7. Tablet A – Accelerated conditions (40°C/75% RH)
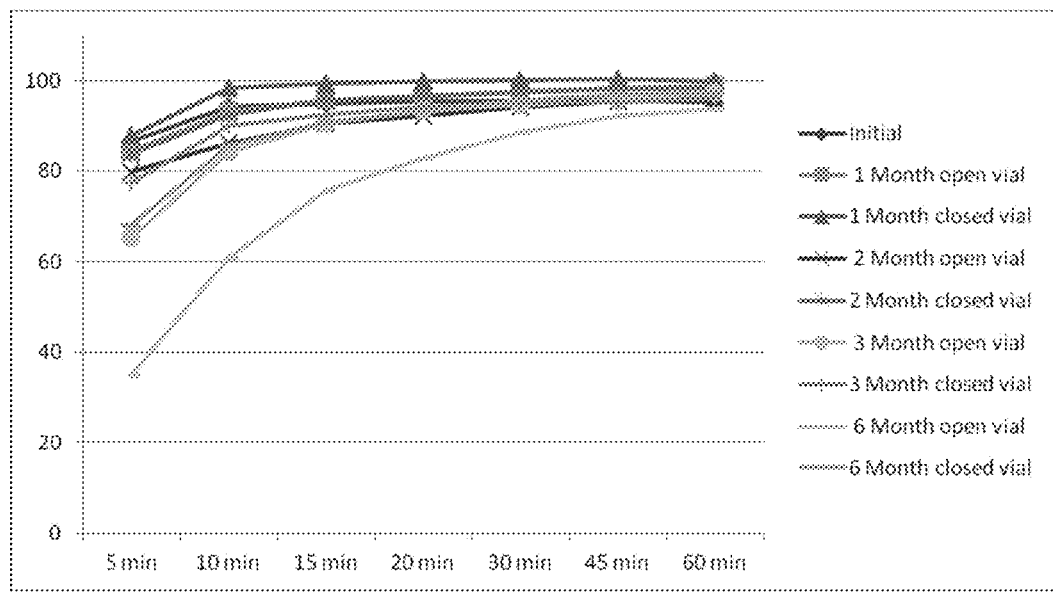

Figure 8. Tablet B – Long term storage conditions (25°C/60% RH)
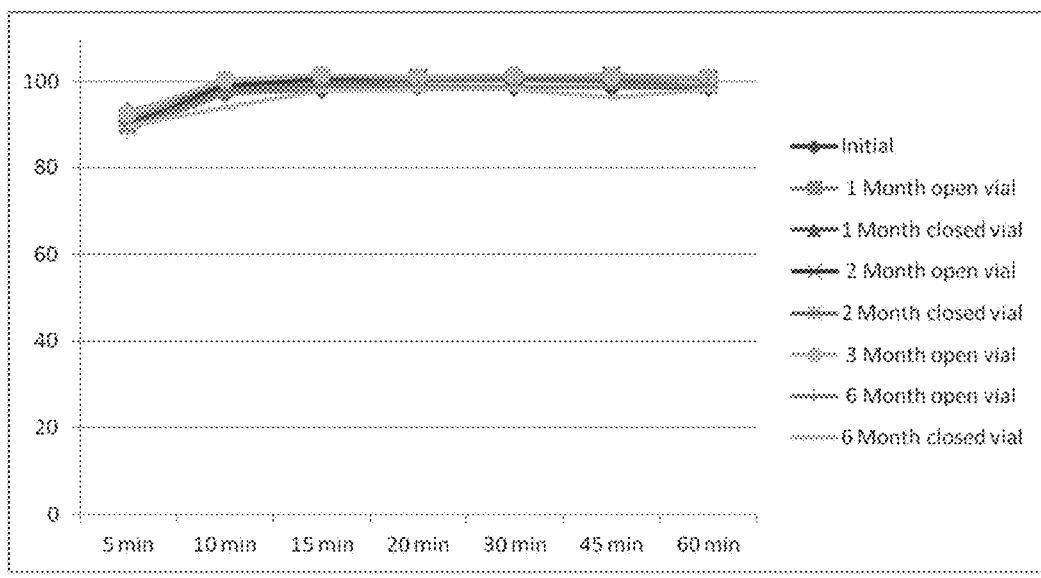
Figure 9. Tablet B – Accelerated conditions (40°C/75% RH)
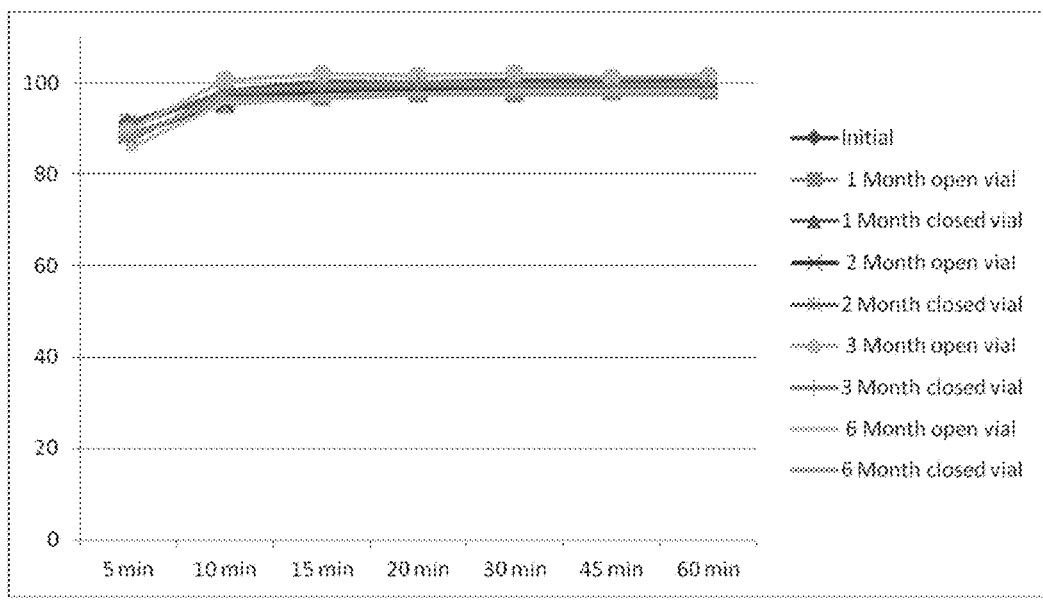

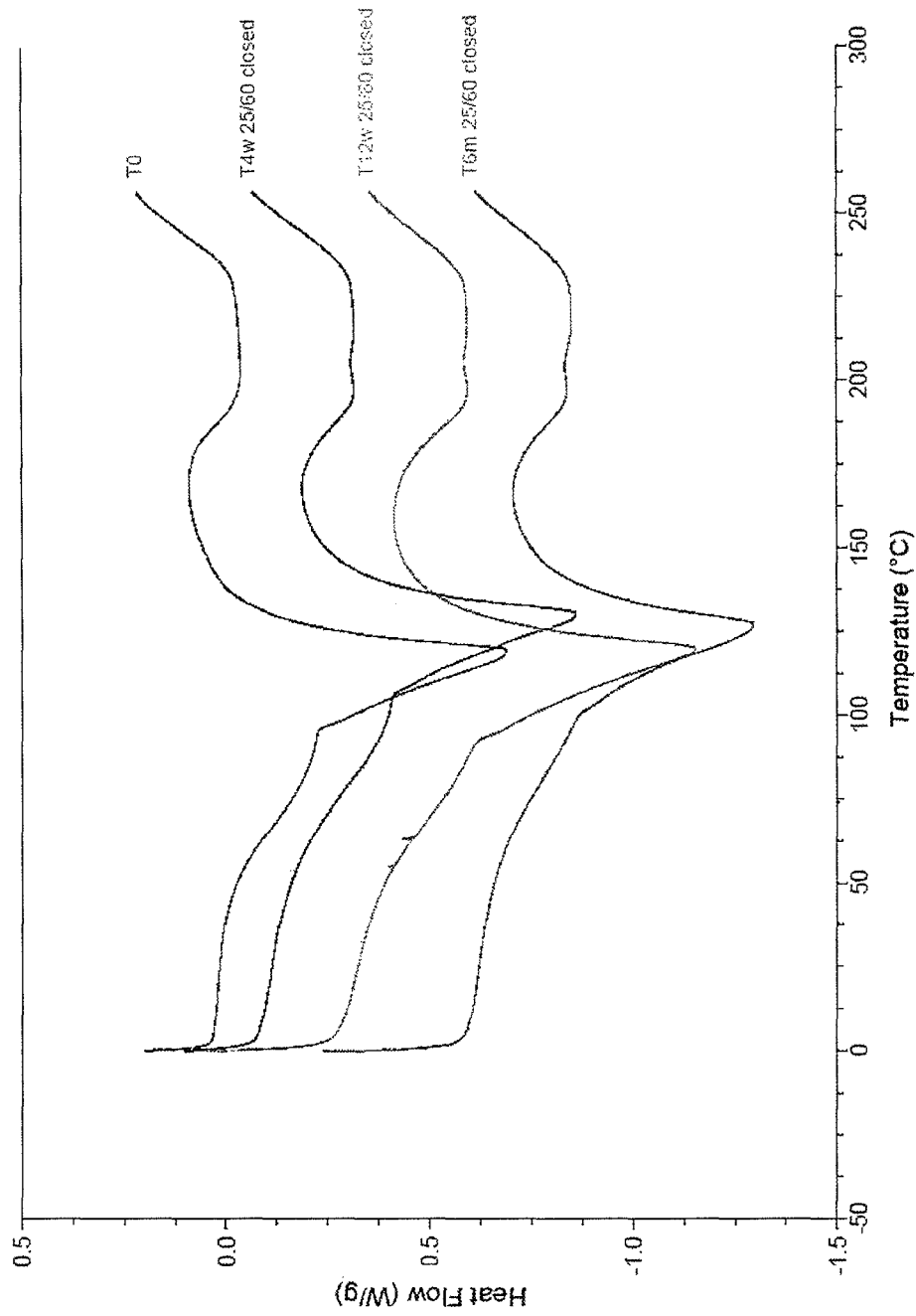
Figure 10. DSC - Tablet A - Long term storage conditions (25°C/60% RH closed vial)

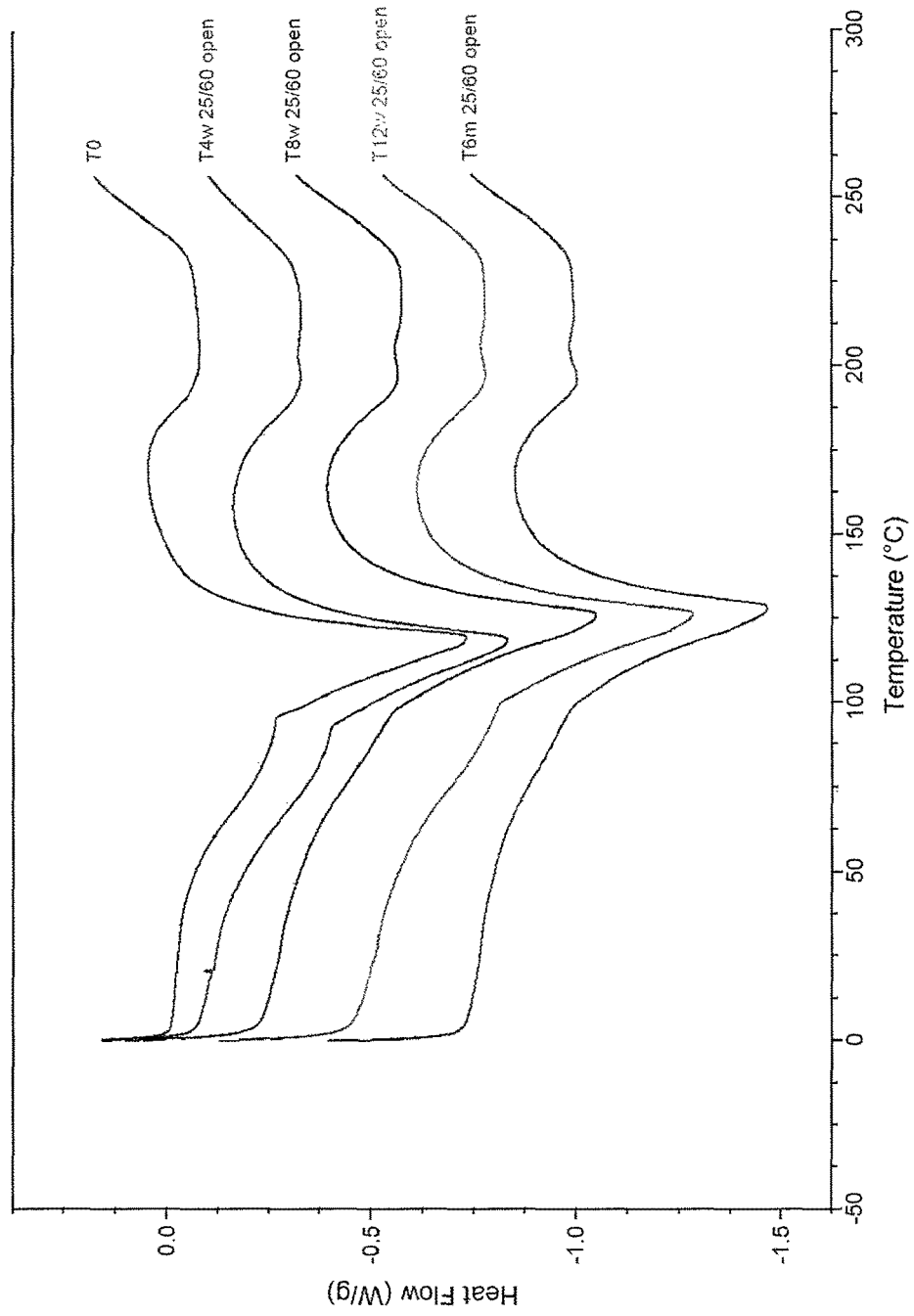
Figure 11. DSC - Tablet A - Long term storage conditions (25°C/60% RH open vial)

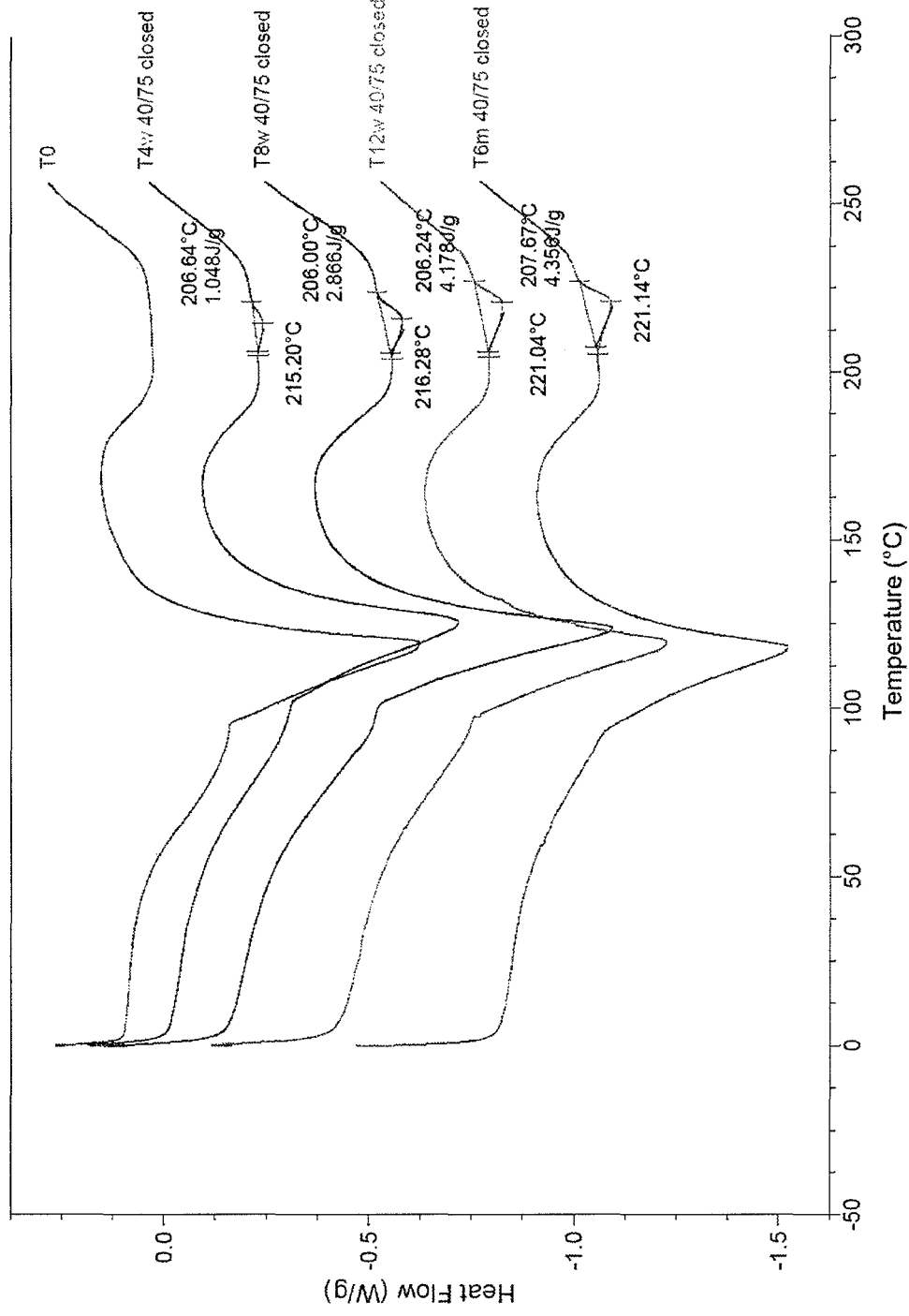
Figure 12. DSC – Tablet A – Accelerated conditions (40°C/75% RH closed vial)

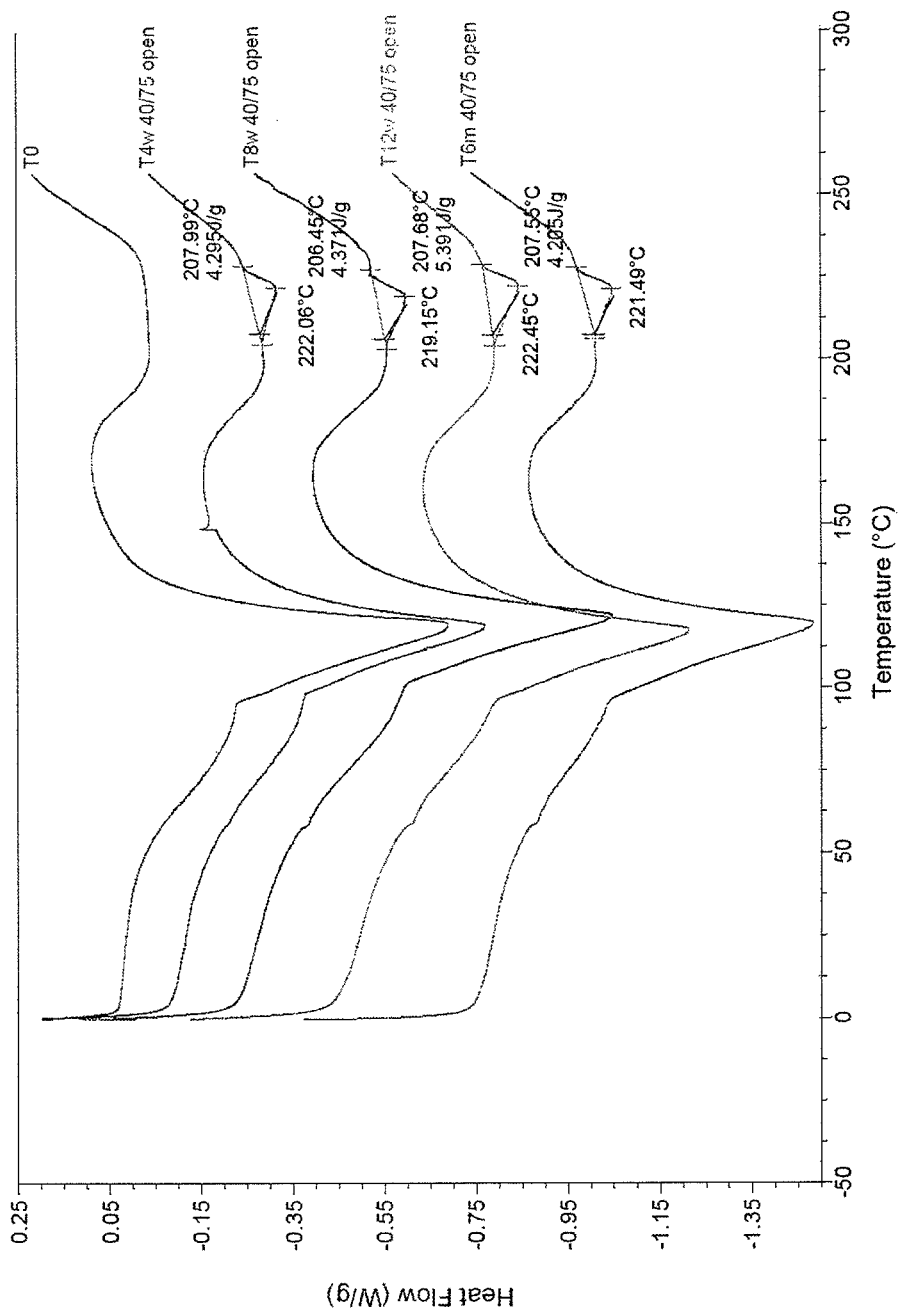
Figure 13.  DSC – Tablet A – Accelerated conditions (40°C/75% RH open vial)

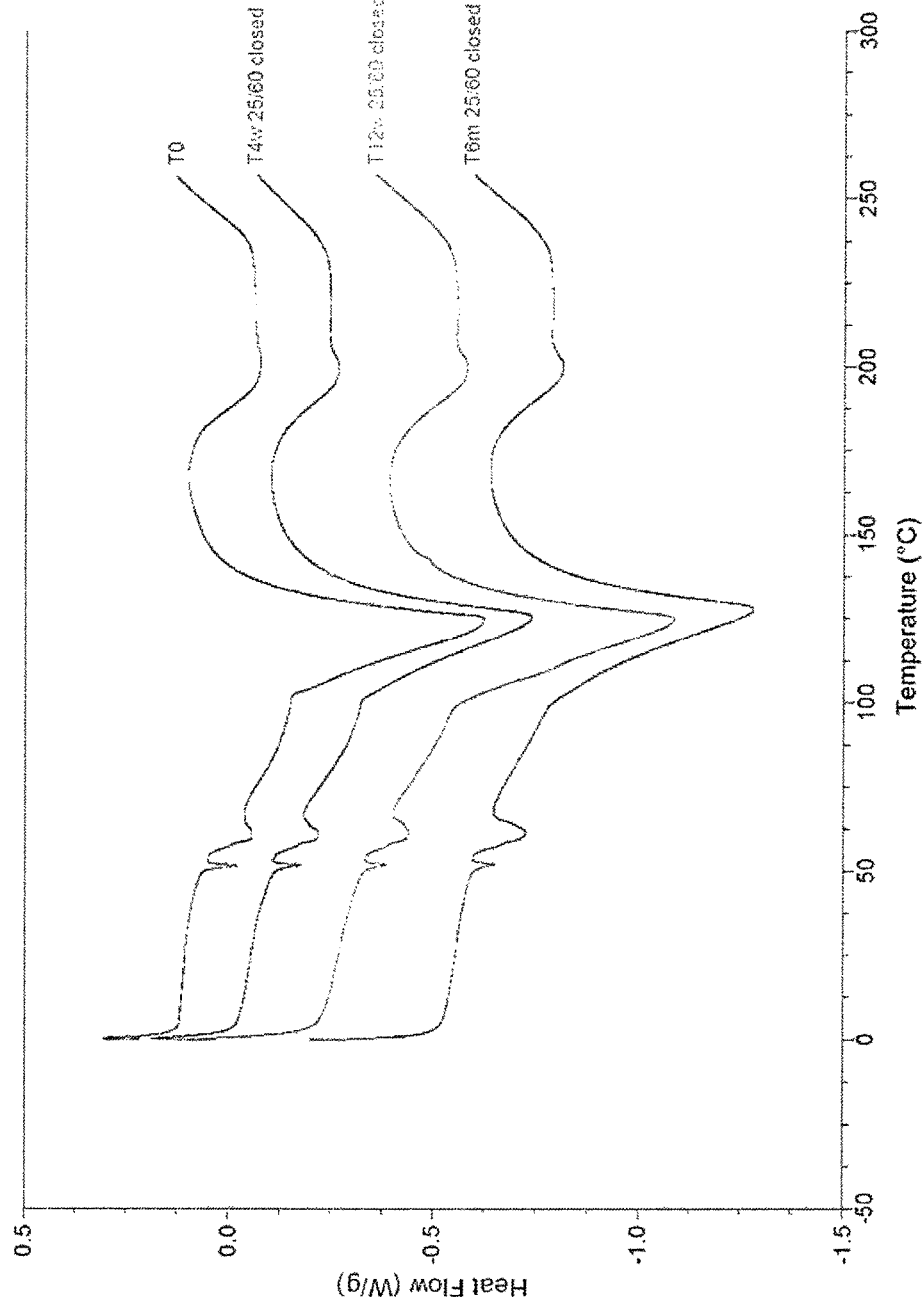
Figure 14. DSC – Tablet B – Long term storage conditions (25°C/60% RH closed vial)

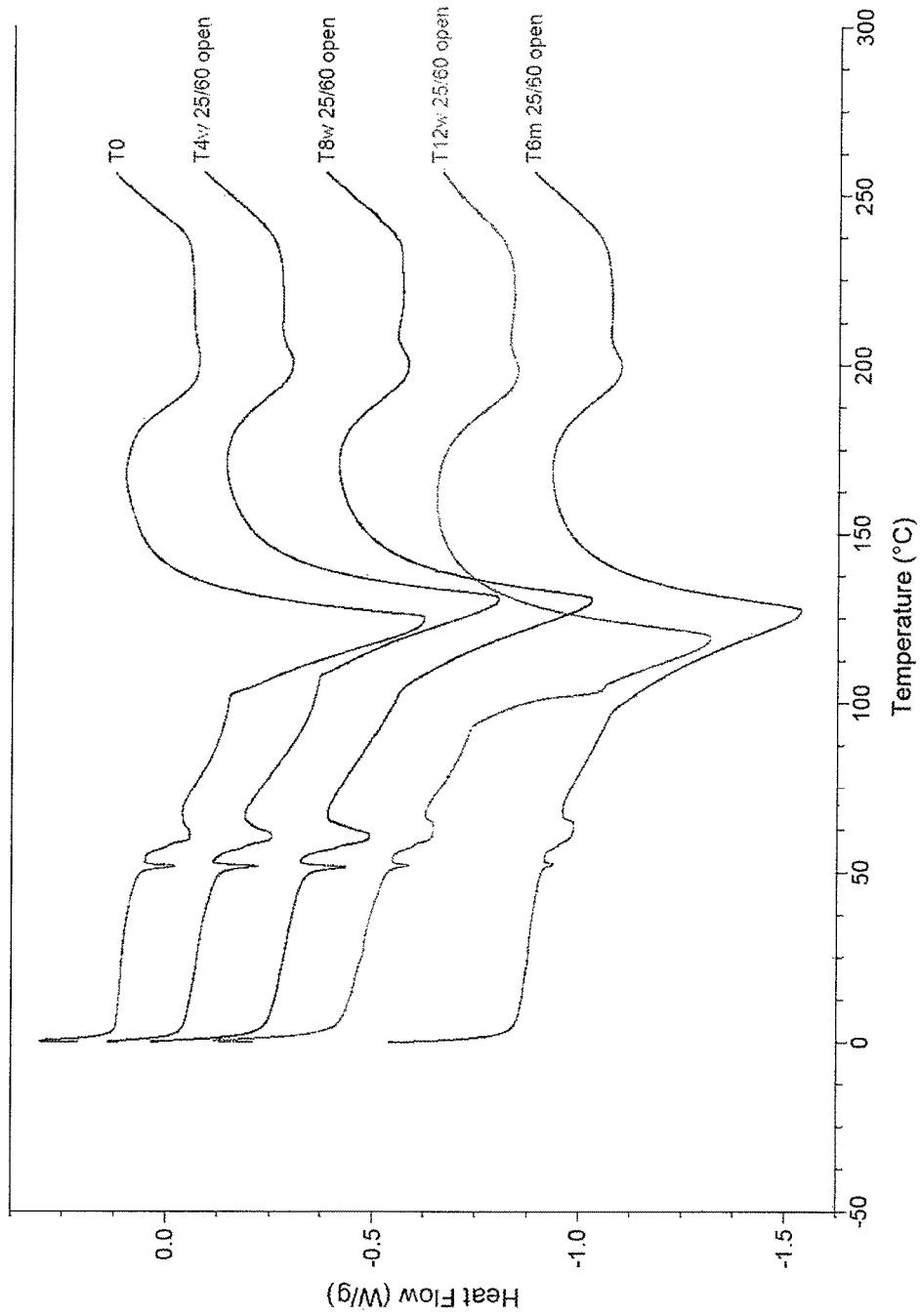
Figure 15. DSC – Tablet B – Long term storage conditions (25°C/60% RH open vial)

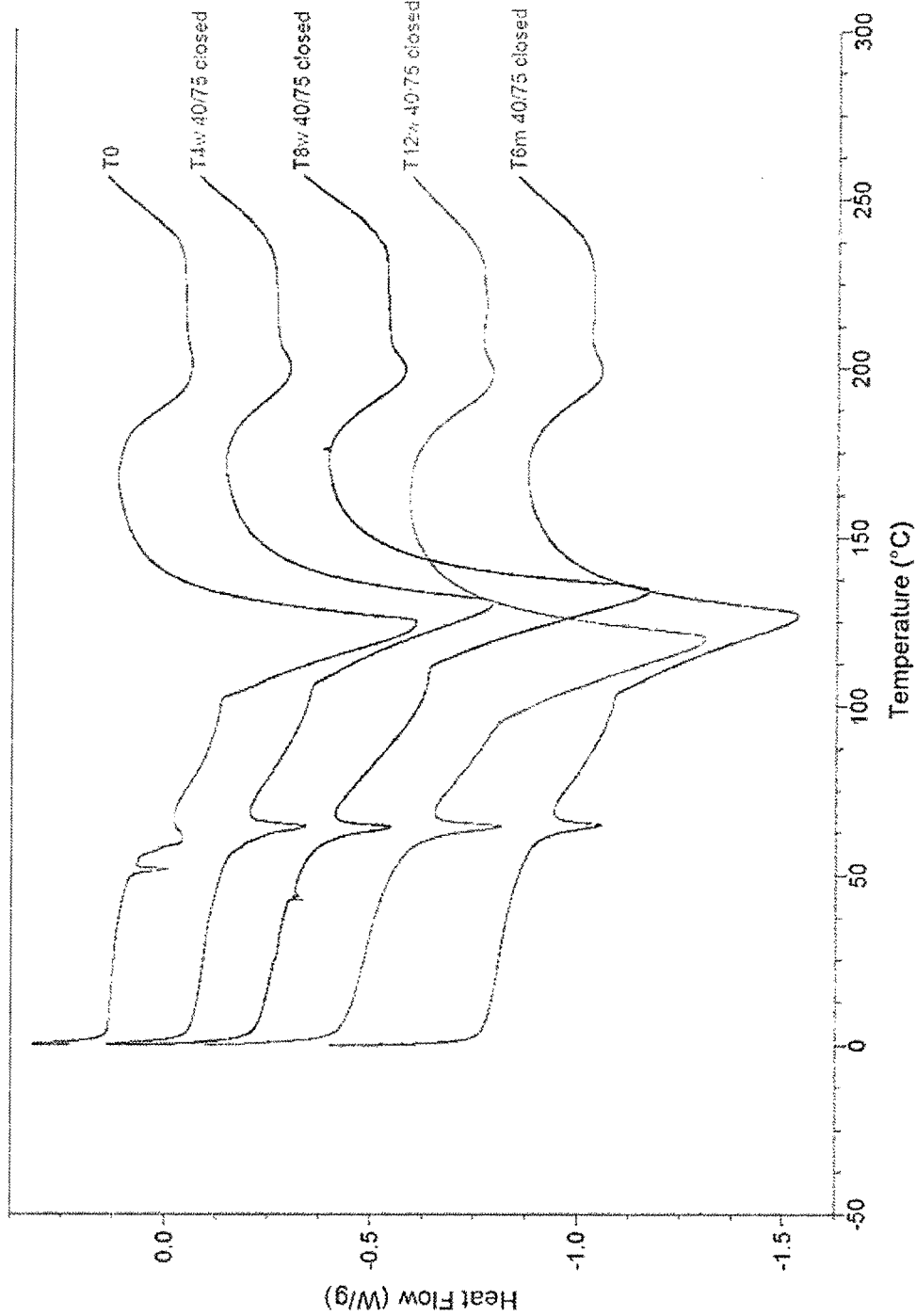
Figure 16. DSC – Tablet B – Accelerated conditions (40°C/75% RH closed vial)

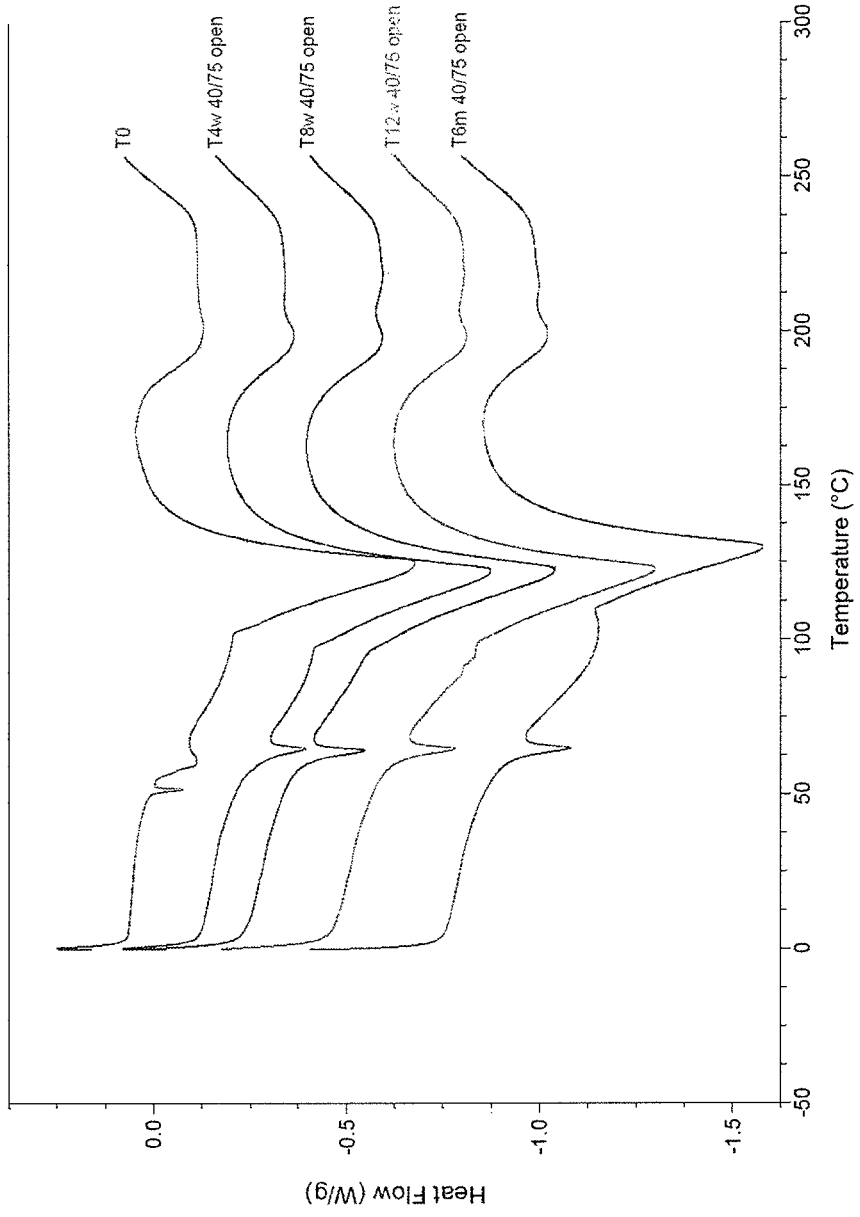
Figure 17. DSC – Tablet B – Accelerated conditions (40°C/75% RH open vial)

PHARMACEUTICAL COMPOSITIONS FOR THE TREATMENT OF INFLAMMATORY DISORDERS

CROSS REFERENCE TO RELATED APPLICATION

The present application claims the priority of co-pending United Kingdom Application No. GB1402070.5 filed on Feb. 7, 2014, and the disclosure of said application is incorporated herein by reference in its entirety. Applicants claim the benefits of said application under 35 U.S.C. § 119.

FIELD OF THE INVENTION

The present invention relates to pharmaceutical compositions containing pharmaceutically acceptable salts of the compound cyclopropanecarboxylic acid {5-[4-(1,1-dioxo-thiomorpholin-4-ylmethyl)-phenyl]-[1,2,4]triazolo[1,5-a]pyridin-2-yl}-amide (Compound 1), and methods for the preparation of such compositions, which are useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. The present invention also provides methods for the prophylaxis and/or treatment of diseases including inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering a pharmaceutical composition of the invention.

BACKGROUND OF THE INVENTION

Current therapies for treating inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, are far from satisfactory and there remains a need to identify new therapeutic agents that may be of use in their treatment. These conditions are chronic conditions which require long term therapy, and repeated intake of the drug. Long term treatment might be a heavy burden on the patient and the practitioner alike, since the patient might be or become intolerant to the drug, and furthermore high dosage, or high dosage frequency may result in uncomfortable side effects, and/or low patient compliance, where the patient may occasionally, deliberately or accidentally, miss a dose. The impact of non-adherence varies across chronic illnesses, and ranges from minimal to very significant (Ingersoll and Cohen, 2008). Therefore, there is a need to identify new agents to reinforce the arsenal of the practitioner, and compounds with low frequency dosage regimen to improve the life of the patients.

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker et al., 2008).

The combination of genetic models and small molecule JAK inhibitor research revealed the therapeutic potential of several JAKs.

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-2, IL-6, IL-4, IL-5, IL-13, or IFNgamma, as well as for other diseases driven by JAK-mediated signal transduction.

In the JAK family members' roles, some overlap exists, since most signaling pathways involve more than one JAK, however for some growth factors such as erythropoietin and thrombopoietin, only JAK2 is involved.

JAK3 plays a major role in blocking immune function via transmission of signals generated by interleukin (IL)-2.

On the other hand, TYK2 would appear to work in combination with JAK2 in order to transduce signaling of cytokines such as IL-12 and IL-23.

The role of JAK enzymes has been mostly studied using mice where each of the JAK family members has been deleted. JAK1 knockout mice exhibit a perinatal lethal phenotype and also have defective lymphoid development and function as a result of defective signaling by cytokines through JAK1. JAK2 deficiency results in embryonic lethality at day 12 as a result of a failure in definitive erythropoiesis. JAK3-deficient mice have severe combined immunodeficiency (SCID) phenotype but do not have non-immune defects (Verstovsek, 2009).

As has been observed with pan JAK inhibitors, non-selective inhibition may be linked to side effects such as anemia, an increased rate of infections, lower neutrophil and lymphocyte counts, a decrease in haemoglobin, and elevated cholesterol levels (Dolgin, 2011).

Therefore, the development of a selective JAK inhibitor would be beneficial in order to minimize such side effects.

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is untreated, it can lead to substantial disability and pain due to loss of joint function and result in shortened life-expectancy. The aim of RA therapy, therefore, is not only to slow down the disease but to attain remission in order to stop the joint destruction and improve quality of life. Besides the severity of the disease outcome, the high prevalence of RA (~0.8% of adults are affected worldwide) means a high socio-economic impact. (O'Dell, 2004; Smolen and Steiner, 2003). JAK1 is implicated in intracellular signal transduction for many cytokines and hormones. Pathologies associated with any of these cytokines and hormones can be ameliorated by JAK1 inhibitors. Hence, several allergy, inflammation and autoimmune disorders might benefit from treatment with compounds described in this invention including rheumatoid arthritis, systemic lupus erythematosus, juvenile idiopathic arthritis, osteoarthritis, asthma, chronic obstructive pulmonary disease (COPD), tissue fibrosis, eosinophilic inflammation, eosophagitis, inflammatory bowel diseases (e.g. Crohn's disease, ulcerative colitis), transplant, graft-versus-host disease, psoriasis, myositis, psoriatic arthritis, ankylosing spondylitis, juvenile idiopathic arthritis, and multiple sclerosis. (Kopf et al., 2010)

Psoriasis is a disease that can affect the skin. The cause of psoriasis is not fully understood but it is believed that it is an immune mediated related disease linked to the release of cytokines, in particular TNFα, which causes inflammation and rapid reproduction of the skin cells. This hypothesis has been corroborated by the observation that immunosuppressant medication can clear psoriasis plaques. (Zenz et al., 2005) Psoriasis can be accompanied by inflammation of the joints, which is known as psoriatic arthritis. Between 10-30% of all people with psoriasis also have psoriatic arthritis. (European Medicine Agency, 2004) Because of its chronic recurrent nature, psoriasis is a challenge to treat. It has recently been demonstrated that inhibition of JAK could result in successful improvement of the psoriatic condition. (Punwani et al., 2012)

Inflammatory bowel disease (IBD) is a group of inflammatory conditions of the colon and small intestine. The major types of IBD are Crohn's disease and ulcerative colitis. Recently, it has been found via genome-wide association (GWAS) studies that T cell protein tyrosine phosphatise (TCPTP) is a JAK/STAT and growth factor receptor phosphatase that has been linked to the pathogenesis of type 1 diabetes, rheumatoid arthritis, and Crohn's disease by GWAS. (Zikherman and Weiss, 2011) Therefore, inhibition of the JAK pathway might provide a way of treating IBD.

JAK family members have been implicated in additional conditions including myeloproliferative disorders (O'Sullivan et al., 2007), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias (e.g. acute myeloid leukaemia (O'Sullivan et al., 2007; Xiang et al., 2008) and acute lymphoblastic leukaemia (Mullighan et al., 2009), cutaneous T-cell lymphoma (Zhang et al., 1996) or solid tumours e.g. uterine leiomyosarcoma (Constantinescu et al., 2008), prostate cancer (Tam et al., 2007) and breast cancer (Berishaj et al., 2007). These results indicate that inhibitors of JAK, in particular of JAK1, may also have utility in the treatment of cancers (leukaemias and solid tumours e.g. uterine leiomyosarcoma, prostate cancer, or pancreatic cancers).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signalling (Naka et al., 2002). This result shows that inhibitors of JAK, may also find utility in the treatment of said diseases.

Thus, compounds which are potent inhibitors of JAK would offer the potential for treating a wide variety of the diseases and conditions described above.

The compound cyclopropanecarboxylic acid {5-[4-(1,1-dioxo-thiomorpholin-4-ylmethyl)-phenyl]-[1,2,4]triazolo[1,5-a]pyridin-2-yl}-amide (Compound 1), which has the chemical structure:

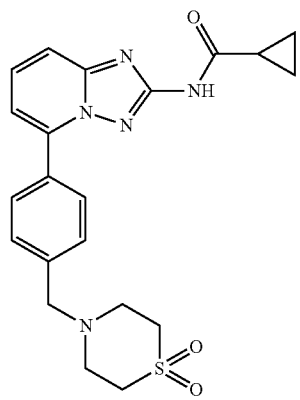

is disclosed in our earlier application WO2010/149769 (Menet and Smits, 2010) as being an inhibitor of JAK and as being useful in the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. The data presented in WO2010/149769 demonstrate that the compound has unexpectedly high in vivo potency compared with structurally similar compounds.

SUMMARY OF THE INVENTION

The present invention provides pharmaceutical compositions of the invention containing pharmaceutically acceptable salts of Compound 1, and in particular the hydrochloric acid salt or a solvate or hydrate of this acid addition salt, useful in the treatment and/or prophylaxis of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. In particular, Compound 1 may act as an inhibitor of JAK, and more particularly of JAK1. The present invention also provides methods for the production of these pharmaceutical compositions of the invention and methods for the treatment and/or prophylaxis of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering the pharmaceutical compositions of the invention.

The experimental examples provided in WO2010/149769 describe the preparation and characterisation of Compound 1 in the form of a free base. It has now been found that presenting the compound as an acid addition salt, and in particular a hydrochloric acid salt or a solvate or hydrate of this acid addition salt, has a beneficial effect on bioavailability.

However, unexpected problems have been encountered with solid dosage forms of salts of Compound 1. Thus, conventional capsule formulations containing a dry mix of a hydrochloride trihydrate salt with microcrystalline cellulose, croscarmellose sodium, colloidal anhydrous silica and magnesium stearate have been found to undergo a significant degree of conversion of the salt back to the free base. This conversion is problematic because the salt and the free base have different dissolution rates which may give rise to variable drug release profiles and variations in bioavailability. The conversion of HCl salt into free base in the capsules was found to be temperature dependent and was not eliminated by the use of high moisture barrier packaging materials such as for example alu-alu blister packs.

The problem is not limited to capsules. Similar problems of conversion to free base upon storage over several months were encountered with tablet formulations containing a conventional disintegrant (croscarmellose sodium) and a conventional lubricant (magnesium stearate): see the comparative examples below.

The applicants have found that by using non-ionic excipients, in particular by replacing magnesium stearate with a non-ionic lubricating agent, and preferably also by replacing the croscarmellose sodium disintegrant with a non-ionic equivalent, the stability of the hydrochloric acid salt of Compound 1 or a solvate or hydrate of this acid addition salt is significantly improved.

Accordingly, in a first aspect, is provided a pharmaceutical composition of the invention comprising:
(i) a hydrochloric acid salt of Compound 1 or a solvate or hydrate of this acid addition salt:

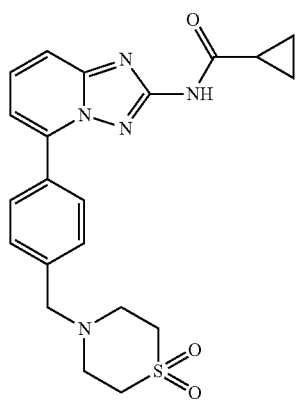

1 and
(ii) an inert solid diluent.

Accordingly, in a second aspect, is provided a pharmaceutical composition of the invention comprising:
(i) a hydrochloric acid salt of Compound 1 or a solvate or hydrate of this acid addition salt;
(ii) an inert solid diluent; and
(iii) a lubricant.

In another aspect, there is provided a pharmaceutical composition of the invention comprising:
(i) a hydrochloric acid salt of Compound 1 or a solvate or hydrate of this acid addition salt;
(ii) an inert solid diluent;
(iii) a lubricant; and
(iv) a non-ionic disintegrant.

In yet another aspect, there is provided a pharmaceutical composition of the invention comprising:
(i) a hydrochloric acid salt of Compound 1 or a solvate or hydrate of this acid addition salt;
(ii) an inert solid diluent;
(iii) a lubricant;
(iv) a non-ionic disintegrant; and
(v) a glidant.

In one embodiment, the pharmaceutical composition is dosed as an enteral formulation. In a particular embodiment, the enteral formulation is a tablet. In another particular embodiment, the enteral formulation is a capsule.

Unless indicated otherwise, references to the weight of the active compound within a formulation as used herein when defining amounts of components, exclude any coatings (e.g. film coating) applied to the tablets.

In one embodiment, the pharmaceutical composition is dosed as an enteral formulation, wherein the dose contains from 1 mg to 500 mg of the hydrochloric acid salt of Compound 1 or a solvate or hydrate of this acid addition salt. In a particular embodiment, the enteral formulation dose contains from 10 mg to 300 mg of the active compound. In a more particular embodiment, the enteral formulation dose contains from 25 mg to 250 mg of the active compound. In a most particular embodiment, the enteral formulation dose contains 10 mg, 20 mg, 25 mg, 50 mg, 75 mg, 100 mg, 150 mg, 200 mg, 250 mg, or 300 mg of the active compound.

In a particular aspect, the pharmaceutical composition of the invention are provided for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In a further aspect, the pharmaceutical compositions of the invention may additionally comprise further therapeutically active ingredients suitable for use in combination with the active compound. In a more particular aspect, the further therapeutically active ingredient is an agent for the treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In a further aspect of the invention, this invention provides a method of treating a mammal, in particular humans, afflicted with a condition selected from among those listed herein, and particularly inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, which method comprises administering an effective amount of the pharmaceutical composition of the invention as described herein.

In additional aspects, this invention provides methods for synthesizing the active compound, with representative synthetic protocols and pathways disclosed later on herein.

Other objects and advantages will become apparent to those skilled in the art from a consideration of the ensuing detailed description.

It will be appreciated that the active compound may be metabolized to yield biologically active metabolites.

BRIEF DESCRIPTION OF THE DRAWINGS

FIG. 1 shows the XRPD spectrum of the [Compound 1.HCl.3H$_2$O] adduct.

FIG. 2 shows the Compound1.HCl.3H$_2$O crystal structure.

FIG. 3 shows the exposure and bioavailability of the free base of Compound 1 compared to its HCl trihydrate salt.

FIG. 4 shows the evolution of the differential scanning calorimetry (DSC) trace of Capsule A under accelerated conditions (40° C./75% relative humidity (RH)).

FIG. 5 shows the evolution of the DSC trace of Capsule B under accelerated conditions (40° C./75% RH).

FIG. 6 shows the evolution of the dissolution rate of Tablet A under long term storage conditions (25° C./60% RH) in open and closed vials.

FIG. 7 shows the evolution of the dissolution rate of Tablet A under accelerated conditions (40° C./75% RH) in open and closed vials.

FIG. 8 shows the evolution of the dissolution rate of Tablet B under long term storage conditions (25° C./60% RH) in open and closed vials.

FIG. 9 shows the evolution of the dissolution rate of Tablet B under accelerated conditions (40° C./75% RH) in open and closed vials.

FIG. 10 shows the evolution of the DSC trace of the Tablet A under long term storage conditions (25° C./60% RH) in closed vial.

FIG. 11 shows the evolution of the DSC trace of the Tablet A under long term storage conditions (25° C./60% RH) in open vial.

FIG. 12 shows the evolution of the DSC trace of the Tablet A under accelerated conditions (40° C./75% RH) in closed vial.

FIG. 13 shows the evolution of the DSC trace of the Tablet A under accelerated conditions (40° C./75% RH) in open vial.

FIG. 14 shows the evolution of the DSC trace of the Tablet B under long term storage conditions (25° C./60% RH) in closed vial.

FIG. 15 shows the evolution of the DSC trace of the Tablet B under long term storage conditions (25° C./60% RH) in open vial.

FIG. 16 shows the evolution of the DSC trace of the Tablet B under accelerated conditions (40° C./75% RH) in closed vial.

FIG. 17 shows the evolution of the DSC trace of the Tablet B under accelerated conditions (40° C./75% RH) in open vial.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

As used herein, the term 'pharmaceutical composition of the invention' means a mixture comprising an pharmaceutically acceptable active ingredient, in combination with suitable pharmaceutically acceptable excipients, wherein the pharmaceutically acceptable ingredient is a pharmaceutically acceptable acid addition salt of the compound cyclopropanecarboxylic acid {5-[4-(1,1-dioxo-thiomorpholin-4-ylmethyl)-phenyl]-[1,2,4]triazolo[1,5-a]pyridin-2-yl}-amide, or a solvate or hydrate of this acid addition salt.

Pharmaceutical excipients are substances other than the pharmaceutically acceptable active ingredient which have been appropriately evaluated for safety and which are intentionally included in an oral solid dosage form. For example, excipients can aid in the processing of the drug delivery system during its manufacture, protect, support or enhance stability, bioavailability or patient acceptability, assist in product identification, or enhance any other attribute of the overall safety, effectiveness or delivery of the drug during storage or use. Examples of excipients include, for example but without limitation inert solid diluents (bulking agent e.g. lactose), binders (e.g. starch), glidants (e.g. colloidal silica), lubricants (e.g. non-ionic lubricants such as vegetable oils), disintegrants (e.g. starch, polivinylpyrrolidone), coating better polymers (e.g. hydroxypropyl methylcellulose), colorants (e.g. iron oxide), and/or surfactants (e.g. non-ionic surfactants). (Rowe et al., 2009)

As used herein, the term 'pharmaceutical formulation' means the process in which different chemical substances, including the active drug, are combined to produce a final medicinal product. Examples of formulation include enteral formulations (tablets, capsules), parenteral formulations (liquids, lyophilized powders), or topical formulations (cutaneous, inhalable).

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. More particularly, such salts are formed with hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, or L-Tartaric acid.

The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The terms 'inert solid diluent' or 'solid diluent' or 'diluents' refer to materials used to produce appropriate dosage form size, performance and processing properties for tablets and/or capsules. An inert solid diluent can be also referred to as filler or filler material. Particular examples of diluents include cellulose powdered, silicified microcrystalline cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, anhydrous, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, or xylitol. More particular examples of diluents include cellulose powdered, silicified microcrystalline cellulose acetate, compressible sugar, corn starch and pregelatinized starch, dextrose, fructose, glyceryl palmitostearate, anhydrous, monohydrate and corn starch, spray dried monohydrate and microcrystalline cellulose, maltodextrin, maltose, mannitol, medium-chain triglycerides, microcrystalline cellulose, polydextrose, sorbitol, starch, pregelatinized, sucrose, sugar spheres, trehalose, or xylitol.

'Lubricant' refers to materials that prevent ingredients from clumping together and from sticking to the tablet punches or capsule filling machine. Lubricants also ensure that tablet formation and ejection can occur with low friction between the solid and die wall. Particular examples of lubricants include canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, or hydrogenated vegetable oil. More particular examples of diluents include glyceryl behenate, glyceryl monostearate, or hydrogenated vegetable oil.

'Disintegrant' refers to material that dissolve when wet causing the tablet to break apart in the digestive tract, releasing the active ingredients for absorption. They ensure that when the tablet is in contact with water, it rapidly breaks down into smaller fragments, facilitating dissolution. Particular examples of disintegrants include alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, or povidone.

The term 'colorant' describes an agent that imparts color to a formulation. Particular examples of colorants include iron oxide, or synthetic organic dyes (US Food and Drug administration, Code of Federal Regulations, Title 21 CFR Part73, Subpart B).

The term 'plasticizing agent' or 'plasticizer' refers to an agent that is added to promote flexibility of films or coatings. Particular examples of plasticizing agent include polyethylene glycols or propylene glycol.

The term 'pigment' in the context of the present invention refers to an insoluble coloring agent.

The term 'film-coating agent' or 'coating agent' or 'coating material' refers to an agent that is used to produce a cosmetic or functional layer on the outer surface of a dosage form. Particular examples of film-coating agent include glucose syrup, maltodextrin, alginates, or carrageenan.

'Glidant' refers to materials that are used to promote powder flow by reducing interparticle friction and cohesion. These are used in combination with lubricants as they have no ability to reduce die wall friction. Particular examples of glidants include powdered cellulose, colloidal silicon dioxide, hydrophobic colloidal silica, silicon dioxide, or talc. More particular examples of glidants include colloidal silicon dioxide, hydrophobic colloidal silica, silicon dioxide, or talc.

'Flavouring agents' refers to material that can be used to mask unpleasant tasting active ingredients and improve the acceptance that the patient will complete a course of medication. Flavourings may be natural (e.g. fruit extract) or artificial. Non limiting examples of flavouring agents include mint, cherry, anise, peach, apricot, liquorice, raspberry, or vanilla.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory diseases' refers to the group of conditions including, rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, Whipple, chronic ulcerative colitis, or colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, and chronic obstructive pulmonary disease (COPD).

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-celllymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor. More particularly, the cancer is selected from breast cancer, endometrial and cervical cancer, lung cancer, ovarian cancer, prostate cancer, hepatic cancer, and pancreatic cancer.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term 'allergy' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'transplant rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving degradation and/or disruption of cartilage homeostasis' includes conditions such as osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

As used herein the term 'disease(s) associated with hypersecretion of interferons' includes conditions such as systemic and cutaneous lupus erythematosis, lupus nephritis, dermatomyositis, Sjogren's syndrome, psoriasis, rheumatoid arthritis.

As used herein the term 'salt(s) of the invention', and equivalent expressions, are meant to embrace pharmaceutically acceptable salts of Compound 1 as herein described.

Other derivatives of Compound 1 have activity in both their acid and acid derivative forms, but in the acid sensitive form often offers advantages of solubility, tissue compatibility, or delayed release in the mammalian organism (Bundgard, H, 1985).

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron, and $^{13}$ Emission Topography (PET) studies for examining substrate receptor occupancy.

All isotopic variants of the compounds provided herein, radioactive or not, are intended to be encompassed within the scope of the invention.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It will be appreciated that compounds of the invention may be metabolized to yield biologically active metabolites.

The Invention

The present invention relates to pharmaceutical compositions containing pharmaceutically acceptable salts of the compound cyclopropanecarboxylic acid {5-[4-(1,1-dioxo-thiomorpholin-4-ylmethyl)-phenyl]-[1,2,4]triazolo[1,5-a]pyridin-2-yl}-amide (Compound 1), and methods for the preparation of such compositions, which are useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. In particular, a pharmaceutical composition inhibits JAK, a family of tyrosine kinases, and more particularly JAK1.

The present invention also provides methods for the prophylaxis and/or treatment of diseases including inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering a pharmaceutical composition of the invention.

Accordingly, in a first aspect, is provided a pharmaceutical composition of the invention comprising:
  (i) a hydrochloric acid salt of Compound 1 or a solvate or hydrate of this acid addition salt:

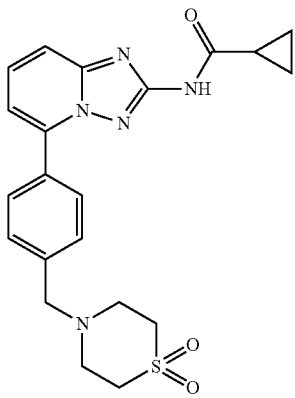

and
(ii) an inert solid diluent.

Accordingly, in a second aspect, is provided a pharmaceutical composition of the invention comprising:
(i) a hydrochloric acid salt of Compound 1 or a solvate or hydrate of this acid addition salt;
(ii) an inert solid diluent; and
(iii) a lubricant.

In another aspect, it is provided a pharmaceutical composition of the invention comprising:
(i) a hydrochloric acid salt of Compound 1 or a solvate or hydrate of this acid addition salt;
(ii) an inert solid diluent;
(iii) a lubricant; and
(iv) a non-ionic disintegrant.

In yet another aspect, it is provided a pharmaceutical composition of the invention comprising:
(i) a hydrochloric acid salt of Compound 1 or a solvate or hydrate of this acid addition salt;
(ii) an inert solid diluent;
(iii) a lubricant;
(iv) a non-ionic disintegrant; and
(v) a glidant.

In another embodiment, the pharmaceutical composition of the invention comprises a hydrochloric acid salt of Compound 1, wherein the salt is a 1:1 [Compound 1:HCl] adduct.

In another embodiment, the pharmaceutical composition of the invention comprises a hydrochloric acid salt of Compound 1, wherein the salt is a solvate of a hydrochloric acid salt of Compound 1. In a particular embodiment, the salt is a hydrate. In a more particular embodiment, the salt is a mono, di, or trihydrate. In a most particular embodiment, the salt is a trihydrate.

In another embodiment, the pharmaceutical composition of the invention comprises a salt of a Compound 1, wherein the salt of the invention is anhydrous.

In one embodiment, the pharmaceutical composition of the invention comprises a hydrochloric acid salt of Compound 1, wherein the salt is a 1:1:1 to 1:1:4 [Compound 1:HCl:H$_2$O] adduct. In a particular embodiment, the pharmaceutical composition of the invention comprises a hydrochloric acid salt of Compound 1, wherein the salt is a 1:1:1, 1:1:2, or 1:1:3 [Compound 1:HCl:H$_2$O] adduct. In a more particular embodiment, the pharmaceutical composition of the invention comprises a hydrochloric acid salt of Compound 1, wherein the salt is a 1:1:3 [Compound 1:HCl:H$_2$O] adduct.

In one embodiment, the pharmaceutical composition of the invention comprises a hydrochloric acid salt of Compound 1, wherein the salt shows peaks on a powder X-ray diffraction spectrum.

In one embodiment, the pharmaceutical composition of the invention comprises a hydrochloric acid salt of Compound 1, wherein the salt is in a solid crystalline form.

In one embodiment, the pharmaceutical composition of the invention comprises a hydrochloric acid salt of Compound 1, wherein the salt is a wherein the salt is a 1:1:3 [Compound 1:HCl:H$_2$O] adduct in a solid crystalline form, characterized at least by a powder X-ray diffraction peak at any one or more of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, 7 and 32.7°2θ±0.2°2θ.

In one embodiment, the pharmaceutical composition of the invention comprises a hydrochloric acid salt of Compound 1, wherein the salt is a 1:1:3 [Compound 1:HCl:H$_2$O] adduct in a solid crystalline form, characterized at least by a powder X-ray diffraction peak at least at 5, 10, 15, 20, 25, 30 or more of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, 7 and 32.7°2θ±0.2°2θ.

In one embodiment, the pharmaceutical composition of the invention comprises a hydrochloric acid salt of Compound 1, wherein the salt is a 1:1:3 [Compound 1:HCl:H$_2$O] adduct in a solid crystalline form, characterized at least by a powder X-ray diffraction peak in all of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, 7 and 32.7°2θ±0.2°2θ.

In one embodiment, the pharmaceutical composition of the invention comprises a hydrochloric acid salt of Compound 1, wherein the salt is a 1:1:3 [Compound 1:HCl:H$_2$O] adduct in a solid crystalline form, characterized by the powder X-Ray diffraction XRPD pattern expressed in terms of 2 theta angles as shown on FIG. 1.

In one embodiment, the 1:1:3 [Compound 1:HCl:H$_2$O] adduct in a solid crystalline form has a particle size of less than 1000 μM, as measured by laser diffraction (Table II). In a particular embodiment, the 1:1:3 [Compound 1:HCl:H$_2$O] adduct in a solid crystalline form has a particle size between 50 μm and 800 μm. In a more particular embodiment, the 1:1:3 [Compound 1:HCl:H$_2$O] adduct in a solid crystalline form has a particle size between 200 μm and 600 μm. In a most particular embodiment, the 1:1:3 [Compound 1:HCl:H$_2$O] adduct in a solid crystalline form has a particle size between 150 μm and 350 μm.

In one embodiment, the hydrochloric acid salt of Compound 1 constitutes from 1-50.1% by weight of the pharmaceutical composition of the invention. In a particular embodiment, the hydrochloric acid salt of Compound 1 constitutes from 1-50%, 5-45%, 10-40%, 15-35%, or 20-30%, by weight of the pharmaceutical composition of the invention. In a most particular embodiment, the hydrochloric acid salt of Compound 1 constitutes from 22.5-27.5% by weight of the pharmaceutical composition of the invention.

In one embodiment, the pharmaceutical composition of the invention comprising the hydrochloric acid salt of Compound 1, comprises less than 2% of any further ionic excipients. In a particular embodiment, the pharmaceutical composition of the invention comprising the hydrochloric acid salt of Compound 1 comprises less than 1% of any further ionic excipients. In a more particular embodiment, the pharmaceutical composition of the invention comprising the hydrochloric acid salt of Compound 1 comprises less than 0.5% of any further ionic excipients. In a most particular embodiment, the pharmaceutical composition of the invention comprising the hydrochloric acid salt of Compound 1 is substantially free of any further ionic excipients.

In one embodiment, the pharmaceutical composition of the invention additionally comprises an inert solid diluent. In a particular embodiment, the inert solid diluent is selected from cellulose powdered, silicified microcrystalline cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, anhydrous, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, and xylitol. In a particular embodiment, the inert solid diluent is selected from cellulose derivatives, lactose, polyols, sugars, dextrin, and starch. In a more particular embodiment, the inert solid diluent is microcrystalline cellulose, mannitol, sorbitol, or lactose. In a most particular embodiment, the inert solid diluent is microcrystalline cellulose.

In one embodiment, the inert solid diluent constitutes from 49.9-99% by weight of the pharmaceutical composition of the invention. In a particular embodiment, the inert solid diluent constitutes from 49.9-94%, 50-99%, 50-90%, 55-85%, 60-80%, or 65-75%, by weight of the pharmaceutical composition of the invention. In a most particular embodiment, the inert solid diluent constitutes from 67.5-72.5% by weight of the pharmaceutical composition of the invention.

The pharmaceutical compositions of the invention typically additionally comprises a lubricant. The lubricant is preferably other than magnesium stearate. More generally, it is preferred that the lubricant is other than an alkali metal salt or alkaline earth metal salt of stearic acid or other fatty acids, carboxylic acids or sulphonic acids. For example, the lubricant may be other than a metal salt of a fatty acid, carboxylic acid or sulphonic acid. In one general embodiment, the lubricant is a non-ionic lubricant. In a particular embodiment, the lubricant is selected from canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, and hydrogenated vegetable oil. In another particular embodiment, the lubricant is selected from vegetable oils, animal oils, polyethyleneglycol, and glycerolesters. In a more particular embodiment, the lubricant is a vegetable oil (e.g. Lubritab®) glycerol dibehenate, or PEG 10,000. In a most particular embodiment, the lubricant is glycerol dibehenate.

In one embodiment, the lubricant constitutes from 0.1-5% by weight of the pharmaceutical composition of the invention. In a particular embodiment, the lubricant constitutes from 0.5-4% by weight of the pharmaceutical composition of the invention. In a more particular embodiment, the lubricant constitutes from 1-3% by weight of the pharmaceutical composition of the invention. In a most particular embodiment, the lubricant constitutes from 1.5-2.5% by weight of the pharmaceutical composition of the invention.

In one embodiment, the pharmaceutical composition of the invention additionally comprises a disintegrant. The disintegrant may be a non-ionic disintegrant. In a particular embodiment, the disintegrant is selected from alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, and povidone. In more particular embodiment, the disintegrant is selected from starch, cellulose, guar gum, and polyvinyl polymers. In another more particular embodiment, the disintegrant is Crospovidone (Polyvinylpolypyrrolidone), pregelatinised starch, or microcrystalline cellulose. In a most particular embodiment, the disintegrant is Crospovidone.

In one embodiment, the disintegrant constitutes from 0.1-10% by weight of the pharmaceutical composition of the invention. In another embodiment, the disintegrant constitutes from 0.1-5% by weight of the pharmaceutical composition of the invention. In a particular embodiment, the disintegrant constitutes from 0.5-4% % by weight of the pharmaceutical composition of the invention. In a more particular embodiment, the disintegrant constitutes from 1-3% % by weight of the pharmaceutical composition of the invention. In a most particular embodiment, the disintegrant constitutes from 1.5-2.5% % by weight of the pharmaceutical composition of the invention.

In one embodiment, the pharmaceutical composition of the invention additionally comprises a glidant. In a particular embodiment, the glidant is selected from powdered cellulose, colloidal silicon dioxide, hydrophobic colloidal silica, silicon dioxide, and talc. In a more particular embodiment, the glidant is silica, colloidal silicon dioxide talc, cellulose, and starch. In a most particular embodiment, the glidant is colloidal silicon dioxide.

In one embodiment, the glidant constitutes from 0.1-1% by weight of the pharmaceutical composition of the invention. In a particular embodiment, the glidant constitutes from 0.1-0.5% by weight of the pharmaceutical composition of the invention. In a more particular embodiment, the glidant constitutes from 0.2-0.3% by weight of the pharmaceutical composition of the invention.

In one embodiment, the invention provides a pharmaceutical composition of the invention comprising:
(i) 1-50% by weight of a 1:1:3 [Compound 1:HCl:H$_2$O] adduct; and
(ii) 50-99% by weight by weight of an inert solid diluent.

In one embodiment, the invention provides a pharmaceutical composition of the invention comprising:
(i) 1-50% by weight of a 1:1:3 [Compound 1:HCl:H$_2$O] adduct;
(ii) 49.9-94% by weight by weight of an inert solid diluent; and
(iii) 0.1-5% by weight of a lubricant.

In another embodiment, the invention provides a pharmaceutical composition of the invention comprising:
(i) 1-50% by weight of a 1:1:3 [Compound 1:HCl:H$_2$O] adduct;
(ii) 49.9-94% by weight of an inert solid diluent;
(iii) 0.1-5% by weight of a lubricant;
(iv) 0.5-5% by weight of a disintegrant; and
(v) 0-1% by weight of a glidant; and optionally
(vi) one or more further pharmaceutically acceptable excipients.

In another embodiment, the invention provides a pharmaceutical composition of the invention comprising:

(i) 10-40% by weight of a 1:1:3 [Compound 1:HCl:H₂O] adduct;
(ii) 55-90% by weight of an inert solid diluent;
(iii) 1-5% by weight of a lubricant;
(iv) 1-4% by weight of a disintegrant; and
(v) 0.1-1% by weight of a glidant; and optionally
(vi) one or more further pharmaceutically acceptable excipients.

In a further embodiment, the invention provides a pharmaceutical composition of the invention comprising:
(i) 15-35% by weight a 1:1:3 [Compound 1:HCl:H₂O] adduct;
(ii) 55-85% by weight of an inert solid diluent;
(iii) 1.5-5% by weight of a lubricant;
(iv) 1.5-3% by weight of a disintegrant; and
(v) 0.2-0.3% by weight of a glidant; and optionally
(vi) one or more further pharmaceutically acceptable excipients.

In another embodiment, the invention provides a pharmaceutical composition of the invention comprising:
(i) 22-35% by weight a 1:1:3 [Compound 1:HCl:H₂O] adduct;
(ii) 57-75% by weight of an inert solid diluent comprising microcrystalline cellulose;
(iii) 1.5-5% % by weight of a hydrogenated vegetable oil lubricant;
(iv) 1.75-2.25% by weight of a cross-linked polyvinylpyrrolidone disintegrant; and
(v) 0.2-0.3% by weight of colloidal silicon dioxide as a glidant; and optionally
(vi) one or more further pharmaceutically acceptable excipients.

In each of the foregoing embodiments, any further pharmaceutically acceptable excipients (vi) will typically be present, if at all, in amounts of less than 50% by weight, more usually less than 30% by weight or less than 20% by weight or less than 15% by weight or less than 10% by weight. In one embodiment, any further pharmaceutically acceptable excipients (vi) are present, if at all, in amounts of less than 10% by weight, for example less than 5% by weight or less than 1 part by weight. In one particular embodiment, there are substantially no further pharmaceutically acceptable excipients (vi) present.

In one embodiment, is provided a pharmaceutical composition of the invention comprising:
(i) about 24.4% by weight of a 1:1:3 [Compound 1:HCl:H₂O] adduct;
(ii) about 71.35% by weight of an inert solid diluent;
(iii) about 2% by weight of a lubricant;
(iv) about 2% by weight of a non-ionic disintegrant; and
(v) about 0.25% by weight of a glidant.

In another embodiment, it is provided a pharmaceutical composition of the invention comprising:
(i) about 32.27% by weight a 1:1:3 [Compound 1:HCl:H₂O] adduct;
(ii) about 60.48% by weight of an inert solid diluent;
(iii) about 5% by weight of a lubricant;
(iv) about 2% by weight of a non-ionic disintegrant; and
(v) about 0.25% by weight of a glidant.

In one embodiment, it is provided a pharmaceutical composition as described above, wherein at least 90% of said composition is dissolved within about 5 minutes after storage for 1 month in an open recipient at 40° C./75% relative humidity, as measured using the paddle method at a speed of 75 rpm at 37±0.5° C. in 0.01 N HCl as dissolution medium.

In one embodiment, it is provided a pharmaceutical composition as described above, wherein at least 95% of said composition is dissolved within about 15 minutes after storage for 1 month in an open recipient at 40° C./75% relative humidity, as measured using the paddle method at a speed of 75 rpm at 37±0.5° C. in 0.01 N HCl as dissolution medium.

While specified groups for each embodiment have generally been listed above separately, this invention is intended to include all combinations of such embodiments within its scope.

While specified groups for each embodiment have generally been listed above separately, the present invention is intended to include all combinations of variables from any of the disclosed embodiments within its scope.

Alternatively, the exclusion of one or more of the specified variables from an embodiment or combinations thereof is also contemplated by the present invention.

A pharmaceutical composition of the invention is administered in a pharmaceutically effective amount, wherein said amount actually administered will typically be determined by a physician, in the light of the relevant circumstances, including the condition to be treated, the chosen route of administration, the actual pharmaceutical composition of the invention administered, the age, weight, and response of the individual patient, the severity of the patient's symptoms, and the like.

The pharmaceutical compositions of this invention are administered by oral route and are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured pills, tablets, capsules or the like.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

Methods of Treatment

In one embodiment, the present invention provides a pharmaceutical composition of the invention, for use in medicine. In a particular embodiment, the present invention provides a pharmaceutical composition of the invention, for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In one embodiment, the present invention provides the use of a pharmaceutical composition of the invention in medicine. In a particular embodiment, the present invention provides the use of a pharmaceutical composition of the invention in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In another embodiment, the present invention provides a pharmaceutical composition of the invention for use in the manufacture of a medicament for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In additional method of treatment aspects, this invention provides methods of prophylaxis and/or treatment of a mammal afflicted with inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, which methods comprise the administration of an effective amount of a pharmaceutical composition of the invention herein described for the treatment or prophylaxis of said condition.

In one embodiment, the present invention provides a pharmaceutical composition of the invention, further comprising another therapeutic agent. In a particular embodiment, the other therapeutic agent is an inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons treatment agent.

In one embodiment, the present invention provides a pharmaceutical composition of the invention, for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In one embodiment, the present invention provides a pharmaceutical composition of the invention, in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In another embodiment, the present invention provides a pharmaceutical composition of the invention for use in the manufacture of a medicament for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In additional method of treatment aspects, this invention provides methods of prophylaxis and/or treatment of a mammal afflicted with inflammatory diseases, which methods comprise the administration of an effective amount of a pharmaceutical composition of the invention herein described for the treatment and/or prophylaxis of said condition. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In one embodiment, the present invention provides a pharmaceutical composition of the invention, for use in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In one embodiment, the present invention provides a pharmaceutical composition of the invention, in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In another embodiment, the present invention provides a pharmaceutical composition of the invention for use in the manufacture of a medicament for use in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a pharmaceutical composition of the invention herein described for the treatment and/or prophylaxis of said condition. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In one embodiment, the present invention provides a pharmaceutical composition of the invention, for use in the prophylaxis and/or treatment of proliferative diseases. In a particular embodiment, the proliferative disease is selected from cancer, and leukemia. In a more particular embodiment, the proliferative disease is selected from breast cancer, endometrial and cervical cancer, lung cancer, ovarian cancer, prostate cancer, hepatic cancer, and pancreatic cancer.

In one embodiment, the present invention provides the use of a pharmaceutical composition of the invention in the prophylaxis and/or treatment of proliferative diseases. In a particular embodiment, the proliferative disease is selected from cancer, and leukemia. In a more particular embodiment, the proliferative disease is selected from breast cancer, endometrial and cervical cancer, lung cancer, ovarian cancer, prostate cancer, hepatic cancer, and pancreatic cancer.

In another embodiment, the present invention provides a pharmaceutical composition of the invention for use in the manufacture of a medicament for use in the prophylaxis and/or treatment of proliferative diseases. In a particular embodiment, the proliferative disease is selected from cancer, and leukemia. In a more particular embodiment, the proliferative disease is selected from breast cancer, endometrial and cervical cancer, lung cancer, ovarian cancer, prostate cancer, hepatic cancer, and pancreatic cancer.

In additional method of treatment aspects, this invention provides methods of prophylaxis and/or treatment of a mammal afflicted with proliferative diseases, which methods comprise the administration of an effective amount of a pharmaceutical composition of the invention herein described for the treatment or prophylaxis of said condition. In a particular embodiment, the proliferative disease is selected from cancer, and leukemia. In a more particular embodiment, the proliferative disease is selected from breast cancer, endometrial and cervical cancer, lung cancer, ovarian cancer, prostate cancer, hepatic cancer, and pancreatic cancer.

In one embodiment, the present invention provides a pharmaceutical composition of the invention for use in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In one embodiment, the present invention provides the use of a pharmaceutical composition of the invention in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In another embodiment, the present invention provides a pharmaceutical composition of the invention for use in the manufacture of a medicament for use in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In additional method of treatment aspects, this invention provides methods of prophylaxis and/or treatment of a mammal afflicted with allergy, which methods comprise the administration of an effective amount of a pharmaceutical composition of the invention herein described for the treatment or prophylaxis of said condition. In a particular embodiment, the allergy is selected from allergic airway disease (e.g. asthma, rhinitis), sinusitis, eczema and hives, as well as food allergies or allergies to insect venom.

In one embodiment, the present invention provides a pharmaceutical composition of the invention for use in the prophylaxis and/or treatment of transplant rejection.

In one embodiment, the present invention provides the use of a pharmaceutical composition of the invention in the prophylaxis and/or treatment of transplant rejection.

In another embodiment, the present invention provides a pharmaceutical composition of the invention for use in the manufacture of a medicament for use in the prophylaxis and/or treatment of transplant rejection.

In additional method of treatment aspects, this invention provides methods of prophylaxis and/or treatment of a mammal afflicted with transplant rejection, which methods comprise the administration of an effective amount of a pharmaceutical composition of the invention herein described for the treatment or prophylaxis of said condition.

In one embodiment, the present invention provides a pharmaceutical composition of the invention for use in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides the use of a pharmaceutical composition of the invention in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In another embodiment, the present invention provides a pharmaceutical composition of the invention for use in the manufacture of a medicament for use in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In additional method of treatment aspects, this invention provides methods of prophylaxis and/or treatment of a mammal afflicted with diseases involving degradation and/or disruption of cartilage homeostasis, which methods comprise the administration of an effective amount of a pharmaceutical composition of the invention herein described for the treatment or prophylaxis of said condition. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides a pharmaceutical composition of the invention for use in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In one embodiment, the present invention provides the use of a pharmaceutical composition of the invention in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In another embodiment, the present invention provides a pharmaceutical composition of the invention for use in the manufacture of a medicament for use in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In additional method of treatment aspects, this invention provides methods of prophylaxis and/or treatment of a mammal afflicted with congenital cartilage malformation(s), which methods comprise the administration of an effective amount of a pharmaceutical composition of the invention herein described for the treatment or prophylaxis of said condition. In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In one embodiment, the present invention provides a pharmaceutical composition of the invention for use in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In one embodiment, the present invention provides the use of a pharmaceutical composition of the invention in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In another embodiment, the present invention provides a pharmaceutical composition of the invention for use in the manufacture of a medicament for use in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In additional method of treatment aspects, this invention provides methods of prophylaxis and/or treatment of a mammal afflicted with disease(s) associated with hypersecretion of IL6, which methods comprise the administration of an effective amount of a pharmaceutical composition of the invention herein described for the treatment or prophylaxis of said condition. In a particular embodiment, the disease(s) associated with hypersecretion of IL6 is selected from Castleman's disease, multiple myeloma, psoriasis, Kaposi's sarcoma and/or mesangial proliferative glomerulonephritis.

In one embodiment, the present invention provides a pharmaceutical composition of the invention for use in the prophylaxis and/or treatment of disease(s) associated with hypersecretion of interferons. In a particular embodiment, the disease(s) associated with hypersecretion of interferons is selected from systemic and cutaneous lupus erythematosus, lupus nephritis, dermatomyositis, Sjogren's syndrome, psoriasis, rheumatoid arthritis.

In one embodiment, the present invention provides the use of a pharmaceutical composition of the invention in the prophylaxis and/or treatment of disease(s) associated with hypersecretion of interferons. In a particular embodiment, the disease(s) associated with hypersecretion of interferons is selected from systemic and cutaneous lupus erythematosus, lupus nephritis, dermatomyositis, Sjogren's syndrome, psoriasis, rheumatoid arthritis.

In another embodiment, the present invention provides a pharmaceutical composition of the invention for use in the manufacture of a medicament for use in the prophylaxis and/or treatment of disease(s) associated with hypersecretion of interferons. In a particular embodiment, the disease(s) associated with hypersecretion of interferons is selected from systemic and cutaneous lupus erythematosus, lupus nephritis, dermatomyositis, Sjogren's syndrome, psoriasis, rheumatoid arthritis.

In additional method of treatment aspects, this invention provides methods of prophylaxis and/or treatment of a mammal afflicted with disease(s) associated with hypersecretion of interferons, which methods comprise the administration of an effective amount of a pharmaceutical composition of the invention herein described for the treatment or prophylaxis of said condition. In a particular embodiment, the disease(s) associated with hypersecretion of interferons is selected from systemic and cutaneous lupus erythematosus, lupus nephritis, dermatomyositis, Sjogren's syndrome, psoriasis, rheumatoid arthritis.

A particular regimen of the present method comprises the administration to a subject suffering from inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, of an effective amount of a pharmaceutical composition of the invention for a period of time sufficient to reduce the level of the aforementioned diseases in the subject, and preferably terminate the processes responsible for said diseases.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 500 mg of the pharmaceutical composition of the invention, with particular doses each providing from about 10 to about 300 mg, more particularly about 25 to about 250 mg, and especially 10 mg, 20 mg, 25 mg, 50 mg, 75 mg, 100 mg, 150 mg, 200 mg, 250 mg, or 300 mg.

When used to prevent the onset of a condition, a pharmaceutical composition of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A pharmaceutical composition of the invention can be administered as the sole active agent or it can be administered in combination with other therapeutic agents that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a pharmaceutical composition of the invention is administered as a medicament. In a specific embodiment, said pharmaceutical composition additionally comprises a further active ingredient.

In one embodiment, a pharmaceutical composition of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a pharmaceutical composition of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a pharmaceutical composition of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a pharmaceutical composition of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a pharmaceutical composition of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a pharmaceutical composition of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a pharmaceutical composition of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a salt of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a salt of the invention is co-administered with another therapeutic agent for the treatment and/or prophylaxis of SLE, particular agents include but are not limited to human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a salt of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a salt of the invention may be administered in combination with other therapies including, but not limited to phototherapy, or photochemotherapy (e.g. psoralen and ultraviolet A phototherapy (PUVA)).

In one embodiment, a salt of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

Compound 1 and its hydrochloride salt can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of Compound 1 and pharmaceutical compositions of the invention. Compound 1 and pharmaceutical compositions of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm) $^1$H NMR spectra were recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 21 mm ID×50 mm L, Waters Acquity UPLC BEH C18 1.7 μm, 2.1 mm ID×30 mm L, or Waters Xterra MS 5 μm C18, 100×4.6 mm. The methods are using either MeCN/H$_2$O gradients (H$_2$O contains either 0.1% TFA or 0.1% NH$_3$) or MeOH/H$_2$O gradients (H$_2$O contains 0.05% TFA). Microwave heating was performed with a Biotage Initiator.

TABLE I

List of abbreviations used in the experimental section:

| Abbreviation | Definition |
|---|---|
| μL | microliter |
| APMA | 4-aminophenylmercuric acetate |
| app t | Apparent triplet |
| ATP | Adenosine-5'-triphosphate |
| AUC | Area Under the Curve |
| bd | Broad doublet |
| bs | Broad singlet |
| BSA | Bovine serum albumine |
| bt | Broad triplet |
| Cat. | Catalytic amount |
| cDNA | copy deoxyribonucleic acid |
| d | doublet |
| DCM | Dichloromethane |
| Desc'd | Described in details |
| DMSO | Dimethylsulfoxide |
| DSC | Differential scanning calorimetry |
| DTT | Dithiothreitol |
| DVS | Dynamic vapor sorption |
| EDTA | Ethylenediaminetetraacetic acid |
| eq. | Equivalent |
| Et$_2$O | Diethyl ether |
| EtOAc | Ethyl acetate |
| EtOH | Ethanol |
| FBS | Fetal bovine serum |
| FT-IR | Fourier transformed Infrared spectroscopy |
| g | gram |
| GVS | Gravimetric Vapour Sorption |
| h | hour |
| HPLC | High pressure liquid chromatography |
| HRP | horseradish peroxydase |
| IL | Interleukin |
| Int | Intermediate |
| kg | kilogram |
| L | liter |
| LC-MS | Liquid Chromatography-Mass Spectrometry |
| LPC | lysophosphatidylcholine |
| m | multiplet |
| MeCN | Acetonitrile |
| MEK | Methyl ethyl ketone |
| MeOH | Methanol |
| mg | Milligram |
| mg | milligram |
| min | minute |
| mL | millilitre |
| mmol | millimoles |
| MMP | Matrix Metallo Proteinase |
| MS Ms'd | Mass measured by LC-MS |
| MW | Molecular weight |
| N.A. | Not available |
| NBS | N-Bromosuccinimide |
| nBuOH | n-Butanol |
| NMR | Nuclear Magnetic Resonance |
| ONPG | Ortho-nitrophényl-β-galactoside |
| Patt | Pattern |
| PBF | phosphate buffered formalin |
| PBS | Phosphate buffered saline |
| PCR | Polymerase chain reaction |
| Pd(PPh$_3$)$_4$ | Tetrakis(triphenylphosphine)palladium(0) |
| Pd/C | Palladium on Carbon 10% |
| Pd$_2$(dba)$_3$ | Tris(dibenzylideneacetone)dipalladium(0) |
| PdCl$_2$dppf | [1,1'-Bis(diphenylphosphino)ferrocene]dichloropalladium(II) |
| PEG | Polyethylene glycol |
| ppm | part-per-million |
| XRPD | Powder X-Ray Diffraction |
| q | quadruplet |
| QrtPCR | quantitative real-time PCR |
| QTL | quantitative trait loci |
| rel vol | Relative volumes |
| RH | Relative humidity |
| RNA | Ribonucleic acid |
| rpm | Rotation per min |
| Rt | retention time |
| RT | Room temperature |
| s | singlet |
| sept | septuplet |
| SS-NMR | Solid state Nuclear Magnetic Resonance |
| t | triplet |
| TBME | tButyl methyl ether |
| TEA | Triethylamine |
| TFA | Trifluoroacetic acid |
| TGA | Thermogravimetric analysis |
| THF | Tetrahydrofuran |

TABLE II

Salt study apparatus

| | |
|---|---|
| Chemical Purity Determination by UPLC | Purity analysis is performed on a Waters Acquity system equipped with a diode array detector and Micromass ZQ mass spectrometer using MassLynx software. |
| Particle Size distribution (PSD) Laser diffraction | PSD was determined using a Sympatec laser diffraction HELOS/BF particle size instrument fitted with RODOS/ASPIROS dry dispersion unit operating at 2.5 Bar with a sled speed of 25 mm/s, a combination of R1 0.1/0.18 μm-35 μm and R3 0.5/0.9 μm-175 μm lenses were used for the determination. Trigger conditions: 1 ms, 0.2%. |
| Thermodynamic Aqueous Solubility by HPLC | Aqueous solubility is determined by suspending sufficient compound in water or buffer to give a maximum final concentration of ≥1 mg · mL$^{-1}$ of the parent free-form of the compound. Quantitation is made by HPLC with reference to a standard calibration curve. The solubility is calculated using the peak areas determined by integration of the peak found at the same retention time as the principal peak in the standard injection. |

TABLE II-continued

| Salt study apparatus | |
|---|---|
| GVS | Sorption isotherms are obtained using a SMS DVS Intrinsic moisture sorption analyser, controlled by SMS Analysis Suite software. The sample temperature is maintained at 25° C. by the instrument controls. The humidity is controlled by mixing streams of dry and wet nitrogen, with a total flow rate of 200 mL/min. The relative humidity is measured by a calibrated Rotronic probe (dynamic range of 1.0-100%% RHRH), located near the sample. The weight change, (mass relaxation) of the sample as a function of % RH is constantly monitored by the microbalance (accuracy ±0.005 mg).<br>Typically 5-20 mg of sample was placed in a pre- tared stainless steel mesh basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range. |
| Polarised Light Microscopy (PLM) | Samples are studied on a Leica DLM polarised light microscope with a digital video camera for image capture. A small amount of each sample is placed on a glass slide, mounted in immersion oil and covered with a glass slip, the individual particles being separated as well as possible. The sample is viewed with appropriate magnification and partially polarised light, coupled to a λ false-colour filter. |
| TGA | TGA data are collected on a Mettler TGA/SDTA 85le equipped with a 34 position auto-sampler. The instrument is temperature calibrated using certified indium. Typically 5-30 mg of each sample is loaded onto a pre-weighed aluminium crucible and is heated at 10° C./min from ambient temperature to 400° C. A nitrogen purge at 50 mL/min is maintained over the sample.<br>The instrument control and data analysis software is STARe v9.10. |
| DSC | The samples are evaluated using a DSC Q2000 V24.8 equipped with a RCS90 refrigerated cooling system (TA Instruments, Leatherhead, UK). Nitrogen is used as the purge gas through the DSC cell (50 mL/min) and the RCS unit (300 mL/min). Samples are run in Tzero aluminium pans closed with a Tzero aluminium lid, supplied by TA Instruments. Mass of sample pan and empty reference pan are taken into account. The experimental method consists in an initial 5 min isothermal equilibration period at 0° C. During the subsequent heating run a 10° C./min heating is applied. Samples are typically measured between 0 and 260° C. Temperature and enthalpic calibration is performed with an indium standard. Data are analyzed using TA Instruments Universal Analysis 2000 V4.7A Software. Melting temperature is reported as the onset temperature. |
| FT-IR | Data were collected on a Nicolet Avatar FT-IR spectrometer with a Smart DurasamplIR accessory and controlled by Omnic software. |
| NMR | $^1$H and $^{13}$C Spectra are obtained using a Varian Unity Inova 400 NMR spectrometer with a 5 mm inverse triple resonance probe operating at 400.12 MHz for proton. Samples were prepared in $d_6$-DMSO, unless otherwise stated. Inverse gated $^{13}$C NMR spectra were obtained using a Bruker DPX300 spectrometer using a DUL $^1$H/$^{13}$C probe operating at 75.46 MHz for carbon. The sample was prepared by dissolving ~50 mg of material in $d_6$-DMSO. A D1 of thirty seconds was employed with 7168 scans. |
| SS-NMR | $^{13}$C Solid-state NMR spectra were recorded using a Varian VNMRS spectrometer operating at 100.56 MHz for $^{13}$C and with a 6 mm (outside diameter) magic-angle spinning (MAS) probe. They were obtained using cross polarisation and MAS with a 30 s recycle delay, 1 ms contact time and at a sample spin-rate of 6.8 kHz. Spectral referencing is with respect to an external sample of neat tetramethylsilane, carried out by setting the high-frequency line from adamantane to 38.5 ppm. Measurements were carried out in air and at ambient probe temperature (~25° C.). The samples were analysed as-received. |
| XRPD | Bruker D2 Phaser<br>X-Ray Powder Diffraction patterns are collected on a Bruker AXS D2 diffractometer using Cu K radiation (30 kV, 10 mA), θ-θ geometry, using a Lynxeye detector form 5-42 2θ.<br>The software used for data collection is DIFFRAC.SUITE and the data are analysed and presented using Diffrac Plus EVA v 13.0.0.2.<br>Data collection:<br>Angular range: 5 to 42 °2θ; Step size: 0.012 °2θ; Collection time: 0.15 seconds per step.<br>Sample Preparation:<br>Samples run under ambient conditions are prepared as flat plate specimens using powder as received without grinding. Approximately 1-2 mg of the sample is lightly pressed on a silicon wafer to obtain a flat surface. |

Synthetic Preparation of the Compound of the Invention

Example 1. Preparation of Compound 1

1.1. Route 1

1.1.1. 4-[4-(4,4,5,5-Tetramethyl-[1,3,2]dioxaborolan-2-yl)-benzyl]-thiomorpholine-1,1-dioxide

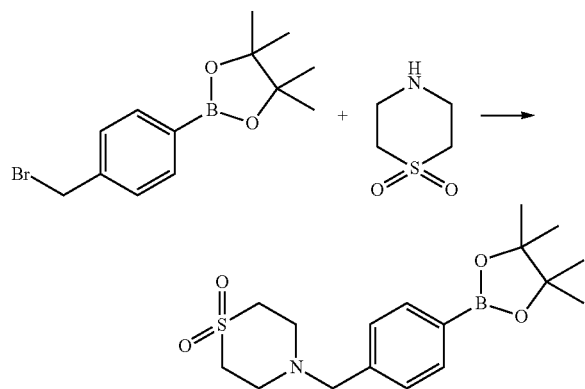

2-(4-Bromomethyl-phenyl)-4,4,5,5-tetramethyl-[1,3,2] dioxaborolane (1 eq) and DIPEA (2 eq) are dissolved in DCM/MeOH (5:1 v:v) under $N_2$ and thiomorpholine 1,1-dioxide (2 eq) is added portionwise. The resulting solution is stirred at room temperature for 16 h. After this time, the reaction is complete. The solvent is evaporated. The compound is extracted with EtOAc and water, washed with brine and dried over anhydrous $MgSO_4$. Organic layers are filtered and evaporated. The final compound is isolated without further purification.

1.1.2. Cyclopropanecarboxylic acid (5-bromo-[1,2,4]triazolo[1,5-a]pyridin-2-yl)-amide

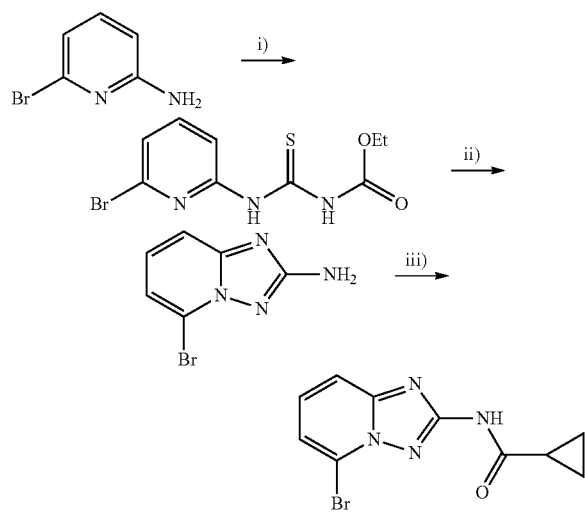

1.1.2.1. Step i): 1-(6-Bromo-pyridin-2-yl)-3-carboethoxy-thiourea

To a solution of 2-amino-6-bromopyridine (1) (253.8 g, 1.467 mol) in DCM (2.5 L) cooled to 5° C. is added ethoxycarbonyl isothiocyanate (173.0 mL, 1.467 mol) dropwise over 15 min. The reaction mixture is then allowed to warm to room temp. (20° C.) and stirred for 16 h. Evaporation in vacuo gives a solid which may be collected by filtration, thoroughly washed with petrol (3×600 mL) and air-dried to afford the desired product. The thiourea may be used as such for the next step without any purification. $^1H$ (400 MHz, $CDCl_3$) δ 12.03 (1H, br s), 8.81 (1H, d), 8.15 (1H, br s), 7.60 (1H, t), 7.32 (1H, dd), 4.31 (2H, q), 1.35 (3H, t).

1.1.2.2. Step ii): 5-Bromo-[1,2,4]triazolo[1,5-a]kyridin-2-ylamine

To a suspension of hydroxylamine hydrochloride (101.8 g, 1.465 mol) in EtOH/MeOH (1:1, 900 mL) is added N,N-diisopropylethylamine (145.3 mL, 0.879 mol) and the mixture is stirred at room temp. (20° C.) for 1 h. 1-(6-Bromo-pyridin-2-yl)-3-carboethoxy-thiourea (2) (89.0 g, 0.293 mol) is then added and the mixture slowly heated to reflux (Note: bleach scrubber is required to quench $H_2S$ evolved). After 3 h at reflux, the mixture is allowed to cool and filtered to collect the precipitated solid. Further product is collected by evaporation in vacuo of the filtrate, addition of $H_2O$ (250 mL) and filtration. The combined solids are washed successively with $H_2O$ (250 mL), EtOH/MeOH (1:1, 250 mL) and $Et_2O$ (250 mL) then dried in vacuo to afford the triazolopyridine derivative (3) as a solid. The compound may be used as such for the next step without any purification.

$^1H$ (400 MHz, DMSO-$d_6$) δ 7.43-7.34 (2H, m, 2×aromatic-H), 7.24 (1H, dd, J 6.8 and 1.8 Hz, aromatic-H), 6.30 (2H, br, $NH_2$);

m/z 213/215 (1:1, M+H$^+$, 100%).

1.1.2.3. Step iii): Cyclopropanecarboxylic acid (5-bromo-[1,2,4]triazolo[1,5-a]pyridin-2-yl)-amide To a solution of the 2-amino-triazolopyridine obtained in the previous step (7.10 g, 33.3 mmol) in dry MeCN (150 mL) at 5° C. is added $Et_3N$ (11.6 mL, 83.3 mmol) followed by cyclopropanecarbonyl chloride (83.3 mmol). The reaction mixture is then allowed to warm to ambient temperature and stirred until all starting material is consumed. If required, further $Et_3N$ (4.64 mL, 33.3 mmol) and cyclopropanecarbonyl chloride (33.3 mmol) is added to ensure complete reaction. Following solvent evaporation in vacuo the resultant residue is treated with 7 N methanolic ammonia solution (50 mL) and stirred at ambient temp. (for 1-16 h) to hydrolyse any bis-acylated product. Product isolation is made by removal of volatiles in vacuo followed by trituration with $Et_2O$ (50 mL). The solids are collected by filtration, washed with $H_2O$ (2×50 mL), acetone (50 mL) and $Et_2O$ (50 mL), then dried in vacuo to give the desired compound.

1.1.2.4. Compound 1

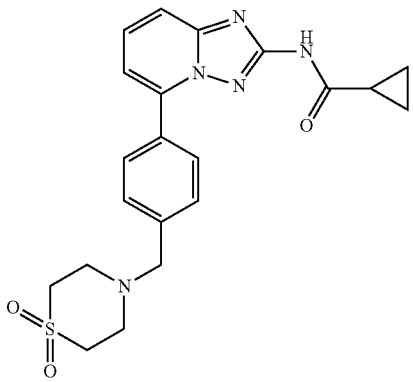 [SMILES: O=C(Nc1nc2cccc(-c3ccc(CN4CCS(=O)(=O)CC4)cc3)n2n1)C1CC1]

4-[4-(4,4,5,5-Tetramethyl-[1,3,2]dioxaborolan-2-yl)-benzyl]-thiomorpholine-1,1-dioxide (1.1 eq.) is added to a solution of cyclopropanecarboxylic acid (5-bromo-[1,2,4]triazolo[1,5-a]pyridin-2-yl)-amide in 1,4-dioxane/water (4:1). $K_2CO_3$ (2 eq.) and $PdCl_2$dppf (0.03 eq.) are added to the solution. The resulting mixture is then heated in an oil bath at 90° C. for 16 h under $N_2$. Water is added and the solution is extracted with ethyl acetate. The organic layers are dried over anhydrous $MgSO_4$ and evaporated in vacuo.

The final compound is obtained after purification by flash chromatography.

Alternatively, after completion of the reaction, a palladium scavenger such as 1,2-bis(diphenylphosphino)ethane, is added, the reaction mixture is allowed to cool down and a filtration is performed. The filter cake is reslurried in a suitable solvent (e.g. acetone), the solid is separated by filtration, washed with more acetone, and dried. The resulting solid is resuspended in water, aqueous HCl is added, and after stirring at RT, the resulting solution is filtered on celite (Celpure P300). Aqueous NaOH is then added to the filtrate, and the resulting suspension is stirred at RT, the solid is separated by filtration, washed with water and dried by suction. Finally the cake is re-solubilised in a mixture of THF/$H_2O$, treated with a palladium scavenger (e.g. SMOPEX 234) at 50° C., the suspension is filtered, the organic solvents are removed by evaporation, and the resulting slurry is washed with water and methanol, dried and sieved, to obtain the title compound as a free base.

1.2. Route 2

1.2.1. Step 1: cyclopropanecarboxylic acid [5-(4-hydroxymethyl-phenyl)-[1,2,4]triazolo[1,5-a]pyridin-2-yl]-amide

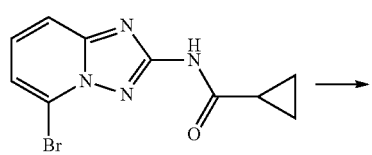

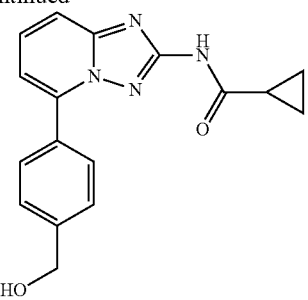

4-(Hydroxymethyl)phenylboronic acid (1.1 eq.) is added to a solution of cyclopropanecarboxylic acid (5-bromo-[1,2,4]triazolo[1,5-a]pyridin-2-yl)-amide in 1,4-dioxane/water (4:1). $K_2CO_3$ (2 eq.) and $PdCl_2$dppf (0.03 eq.) are added to the solution. The resulting mixture is then heated in an oil bath at 90° C. for 16 h under $N_2$. Water is added and the solution is extracted with ethyl acetate. The organic layers are dried over anhydrous $MgSO_4$ and evaporated in vacuo. The resulting mixture is used without further purification.

1.2.2. Step 2: Cyclopropanecarboxylic acid [5-(4-bromomethyl-phenyl)-[1,2,4]triazolo[1,5-a]pyridin-2-yl]-amide

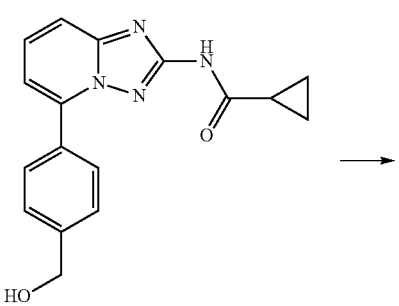

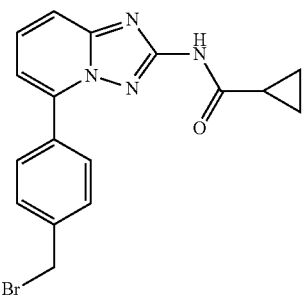

To a solution of cyclopropanecarboxylic acid [5-(4-hydroxymethyl-phenyl)-[1,2,4]triazolo[1,5-a]pyridin-2-yl]-amide (1.0 eq) in chloroform is slowly added phosphorus tribromide (1.0 eq.). The reaction mixture is stirred at room temperature for 20 hours, quenched with ice and water (20 mL) and extracted with dichloromethane. The organic layer is dried over anhydrous $MgSO_4$, filtered and concentrated to dryness. The resulting white residue is triturated in dichloromethane/diethyl ether 2:1 to afford the expected product as a white solid.

Step 3

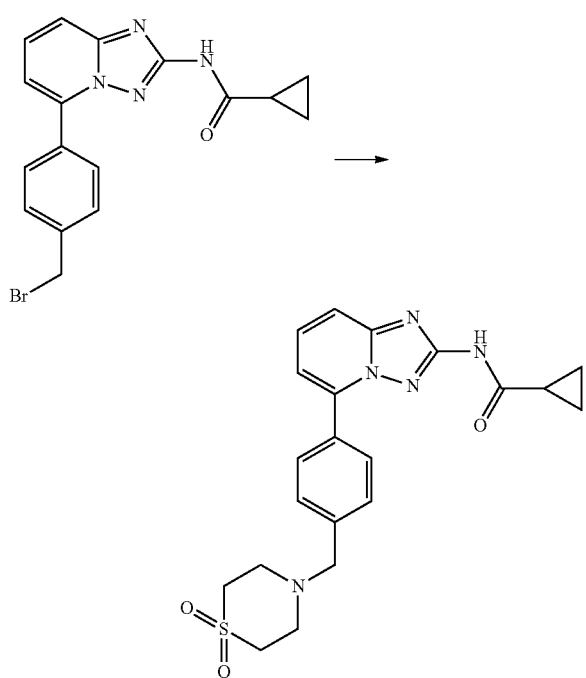

Cyclopropanecarboxylic acid [5-(4-bromomethyl-phenyl)-[1,2,4]triazolo[1,5-a]pyridin-2-yl]-amide (1 eq) and DIPEA (2 eq) are dissolved in DCM/MeOH (5:1 v:v) under $N_2$ and thiomorpholine 1,1-dioxide (1.1 eq) is added dropwise. The resulting solution is stirred at room temperature for 16 h. After this time, the reaction is complete. The solvent is evaporated. The compound is dissolved in DCM, washed with water and dried over anhydrous $MgSO_4$. Organic layers are filtered and evaporated. The final compound is isolated by column chromatography using EtOAc to afford the desired product.

Method of Forming a Hydrochloric Acid Salt

HCl (1 M solution in THF) (655 µl, 0.65 mmol, 1.1 eq.) is added to a stirred suspension of Compound 1 (252.6 mg, 0.59 mmol, 1 eq.) and methanol (5.05 mL, 20 vols) at 50° C. The mixture is cooled to 25° C. at 1° C./min and stirred at 25° C. for 22 h. The solid is isolated by vacuum filtration and dried under suction. XRPD analysis confirmed the formation of a stable non-hygroscopic salt, containing 4-5% water, having an aqueous solubility measured at 1.9 mg/mL Example 2. Large Scale HCl.trihydrate Salt Formation 2.1. Protocol 1

To Compound 1 (45 g, 106 mmol, 1 equiv) under inert atmosphere is added DCM (675 mL) and methanol (225 mL). The resulting suspension is heated to 35° C. under stirring, and trimercaptotriazine trisodium salt 15% in water (22.5 g, 14 mmol, 0.13 eq) is added, and the resulting solution is stirred for 5 h, after which the solution is filtered on 0.45 µm paper under nitrogen pressure.

To the filtrate is added water (50 mL), and the resulting biphasic mixture is stirred at 35° C. for 15 min, after which period the phases are separated, and the organic layer is allowed to cool down to 20° C., and washed twice more with 50 mL water.

The organic layer is cooled down to 15-20° C., then HCl 10% in methanol (42.4 g, 116 mmol, 1.10 eq.) is added over 30 min, causing the precipitation of a solid. The suspension is further stirred at 20° C. for 3 h, then the precipitate is isolated by filtration, the cake is washed with methanol (2×50 mL) to afford the desired product, which is dried under vacuum at 45° C. for 3 h.

2.2. Protocol 2

2.2.1. Step 1: Compound 1.HCl.MeOH

To Compound 1 (100 g, 235 mmol, 1 eq.) suspended in DCM (1.5 L), is added MeOH (0.5 L), and the resulting solution is heated to 35° C. Trimercaptotriazine trisodium 85% (8.7 g, 3 mmol, 0.13 eq.) in water (42 mL) is added and the resulting mixture is stirred at 35° C. for at least 5 h. The solution is then filtered on a 0.45 µm paper filter under nitrogen pressure.

To the resulting solution is added water (150 g), stirred at 35° C. for 15 to 30 min, and the biphasic mixture is separated. The organic layer is washed again twice with water (2×150 g).

Finally, MeOH.HCl (10% w/w) (141 g) is added, and the suspension is stirred at 20° C. for 3 h, and the resulting solid is separated by filtration, the cake is washed with MeOH (2×118 g), dried under vacuum for 3 h at 45° C., to afford Compound 1.HCl.MeOH.

2.2.2. Step 2: Compound $1.HCl.3H_2O$

To formic acid (200 g, 1.6 eq) in water (36 g, 0.4 eq.) is added Compound 1.HCl.MeOH (100 g, 1 eq.) obtained in Step 1 above. The resulting mixture is heated to 55° C. under stirring, and the solution is filtered through a 0.45 µm filter cartridge. Formic acid 85% aq (200 g) is added, and the mixture is cooled to 28-32° C. under gentle stirring.

Water (100 g) is then added, followed with Compound $1.HCl.3H_2O$ (1 g) causing the precipitation of Compound $1.HCl.1.5HCO_2H$.

Under stirring at 28-32° C., water (2 L) is added portionwise in 8 portions of 100 mL, 1 portion of 200 mL, and 2 portions of 500 mL.

The resulting suspension is then filtered, the cake is washed with water (2×100 mL) and dried at 30-35° C. to yield Compound $1.HCl.3H_2O$.

The solid obtained are analysed by XRPD.

TABLE III

| Compound 1. HCl•$H_2O$ Polymorph peaks (FIG.1) | |
|---|---|
| Angle (2θ°) | Intensity (%) |
| 7.3 | 61.4 |
| 8.4 | 35.3 |
| 8.8 | 62.8 |
| 10.7 | 26.3 |
| 12.0 | 22.5 |
| 12.2 | 18.1 |
| 13.2 | 23.6 |
| 13.7 | 16.1 |
| 14.5 | 14.0 |
| 16.3 | 31.0 |
| 16.7 | 100.0 |
| 17.6 | 11.3 |

TABLE III-continued

Compound 1. HCl•H$_2$O Polymorph peaks (FIG.1)

| Angle (2θ°) | Intensity (%) |
|---|---|
| 19.3 | 20.8 |
| 20.2 | 87.5 |
| 20.6 | 16.4 |
| 21.0 | 18.0 |
| 21.4 | 52.0 |
| 21.8 | 58.8 |
| 22.8 | 45.0 |
| 23.4 | 57.5 |
| 23.9 | 10.6 |
| 24.5 | 10.8 |
| 25.2 | 21.7 |
| 25.7 | 35.3 |
| 25.9 | 33.1 |
| 26.4 | 11.7 |
| 27.2 | 13.0 |
| 27.7 | 16.6 |
| 28.3 | 10.8 |
| 28.6 | 19.3 |
| 28.9 | 17.2 |
| 29.2 | 20.2 |
| 29.6 | 47.6 |
| 32.7 | 26.1 |

2.2.2.1. Compound 1.HCl.3H2O Single Crystal X-Ray Diffraction (FIG. 2)

Compound 1.HCl.3H$_2$O is recrystallized from acetone:water (1:1). The results are disclosed in Table IV below.

TABLE IV

Single Crystal structure of Compound 1. HCl•3H$_2$O

| | |
|---|---|
| Molecular formula | C$_{21}$H$_{24}$N$_5$O$_3$S•Cl•3(H$_2$O) |
| Molecular weight | 516.02 |
| Crystal system | Monoclinic |
| Space group | P2$_{1/n}$  a 13.1388(4) Å  α 102.089(2)° |
| | b 8.9437(3) Å  β |
| | c 21.6376(9) Å  γ |
| V | 2486.24(15) Å$^3$ |
| Z | 4 |
| Dc | 1.379 mg/m$^3$ |
| μ | 0.284 mm$^{-1}$ |
| Source | Mo-Kα, 0.71073 Å |
| F(000) | 1088 |
| T | 120(2) K |
| Crystal | colourless prism, 0.39 × 0.16 × 0.12 mm |
| θ range for data collection | 2.982-27.483° |
| Completeness | 99.3% |
| Reflections | 21028 |
| Unique reflections | 5649 |
| R$_{int}$ | 0.0307 |

Refinement method is based on Full-matrix least-squares on F$^2$. R[F$^2$>2σ(F$^2$)]=0.0377 and wR(F$^2$)=0.0837. Goodness of fit (S)=1.109. The refinement method used 5649 reflections, 339 parameters and 0 restraints. All hydrogen positions were identified using the difference map and those attached to C atoms & N atoms were then placed in calculated positions and refined using a riding model. Those hydrogen's attached to the water oxygen's and nitrogen were freely refined. The final $\Delta_{\rho max}$=0.314 e Å$^{-3}$ and $\Delta_{\rho min}$=−0.368 e Å$^{-3}$.

The crystal structure of Compound 1.HCl.3H2O (FIG. 2), shows the unexpected inclusion of the water molecules in the crystal lattice which may provide further stabilisation of the system.

Example 3. PK/PD Study

3.1. Dog Bioavailability Study

3.1.1. Experimental Set Up

The aim of this experiment is to compare the PK in healthy male beagle dogs (3 dogs per group) after a single oral administration of Compound 1 as free base or as a salt formulated as capsules of two different strengths (25 and 100 mg).

The dogs are not fasted before dosing, and have free access to water. Every day of the treatment, a half food ration is provided after the T0 blood sampling, 8 to 17 min before treatment, and the second half ration is given just after dosing or 1 h after treatment for period 2. A 3 days washout period is ensured between treatments.

Compound 1 as a salt or as a free base is administered to a target dose of 10 mg/kg in capsules (either 4×25 mg, or 1×100 mg capsule). The capsule composition is described in the table below.

TABLE V 25 and 100 mg capsules composition

| Component | 25 mg capsule | 100 mg capsule |
|---|---|---|
| Compound 1 | 25.325 mg | 101.3 mg |
| Acdisol (crosscarmelose sodium) | 4 mg | 4 mg |
| Aerosil (colloidal silicon dioxide) | 1 mg | 1 mg |
| Avicel (microcrystalline cellulose) | 243.1 mg | 71 mg |
| Magnesium stearate | 1 mg | 1 mg |

The capsules are administered orally with water (5-10 mL), to provide good oesophageal transit. Each animal is checked at least once daily.

Blood is collected from the jugular vein into lithium heparinised tubes at T0 (before food administration) and then at 1 h, 2 h, 4 h, 6 h, 8 h, 10 h, and 24 h post treatment. Plasma is then obtained from blood by centrifugation (2500 g for 10 min at 4° C.), and stored at −20° C. until analysis.

3.1.2. Plasma Analysis

Representative aliquots of plasma are diluted with control dog plasma as necessary to ensure the concentrations present are within the range of the calibration curve, and extracted by protein precipitation with 2 volumes of acidified (with 0.1% formic acid) acetonitrile containing deuterated Compound 1 as internal standard (at 150 ng/mL).

After vortex mixing and centrifugation at 4° C., the supernatants are diluted with a 0.5 volume of HPLC grade water in a midi-eppendorf 96-well plate. The plate is sealed and shaken to ensure sample homogeneity prior to analysis. Samples are assayed for Compound 1 by LC-MS/MS using a Waters TQS mass spectrometer, against a series of matrix matched calibration and quality control standards.

The Waters TQS method has a standard curve range of 1.00 ng/mL (lower limit of quantitation for undiluted samples), to maximally 4000 ng/mL for Compound 1.

Pharmacokinetic analysis is performed using WinNonlin™ software version 5.3, using concentrations from individual animals. Non-compartmental analysis is applied to determine the PK parameters ($C_{max}$, $T_{max}$, $AUC_{0-last}$, $t_{1/2}$, etc . . . )

Concentrations below the limit of detection are set to zero for descriptive statistics and PK parameter calculations.

The actual doses of Compound 1 administered to each dog are used for dose normalisation of PK parameters ($C_{max}$ and AUC).

3.1.3. Results

Following the protocol above, the following results are obtained:

| Compound form | Free base | | HCl•trihydrate | |
|---|---|---|---|---|
| Dose (single oral administration) | 25 mg/kg | 100 mg/kg | 25 mg/kg | 100 mg/kg |
| Exposure AUC (µg · h/mL) | 10.4 | 11.1 | 33.6 | 21.7 |
| Tmax (h) | 6.0 | 8.0 h | 2.0 | 2.0 |
| Cmax (µg/mL) | 0.894 | 0.797 | 3.05 | 2.63 |
| $T_{1/2}$ (h) | | Range 4.43-8.96 | | |

Compound 1 (as a free base) is taken orally an therefore passes through the HCl containing acidic gastric route, where Compound 1.HCl should be formed. The skilled person would therefore expect to see no difference between the two administered forms.

However, as illustrated on FIG. 14, on average and at the 2 capsule strengths, Compound 1.HCl.3H$_2$O is more rapidly absorbed, and shows in vivo improved exposure over Compound 1, which may result in lower dosage regimen, and thereby improved patient compliance, and potentially lower toxicity, or drug-drug interaction problems.

Example 4. Compound 1. HCl.3H$_2$O Stability Study

4.1. Accelerated Stability Study

4.1.1. Protocol

Samples of [Compound 1. HCl.3H$_2$O] are stored under conditions to evaluate chemical stability and physical stability as described in the table below:

TABLE VI

| Experimental conditions | |
|---|---|
| Chemical stability conditions | Physical stability conditions |
| 25° C./60% RH/Open recipient | RT/<5% RH/Open recipient |
| 40° C./75% RH/Open recipient | RT/56% RH/Open recipient |
| 50° C./Closed recipient | RT/75% RH/Open recipient |

Samples are taken at T0, then every month up to 3 months, and analysed by FT-IR, DSC, and XRPD.

4.1.2. Results

When tested according to the protocol described above, Compound 1. HCl.3H$_2$O is stable under all conditions over the 3 months, and no change in crystallinity is observed.

Example 5. Compound 1. HCl.3H$_2$O Stability Study

5.1. Preparation of the Pharmaceutical Compositions of the Invention

5.1.1. Capsules

5.1.2. Capsule formation

The capsules (Hard gelatin capsules Swedish Orange OP.C307, size 0, Coni-Snap, Capsugel, lot 33234201) are prepared according to the following progressive blending procedure, using a Turbula blender Type T2A (Willy A. Bachofen, Basel, Switzerland):

half of the total amount of filler: 5 min
Compound 1 free base or salt: 20 min
half of the total amount of filler+disintegrant: 10 min
lubricant: 5 min Capsule filling is performed using a Feton capsule filling apparatus in a size 0 capsule.

The capsule contents are presented below in Table VII and 0.

The capsules are then kept for 8 weeks in accelerated stability conditions (40° C./75% RH), and the content is analysed by DSC at regular interval timepoints.

TABLE VII

| Capsule A Composition (ionic) | | | |
|---|---|---|---|
| Component | Function | Eq. 100 mg | Quantity per capsule |
| Compound 1 | Active ingredient | 41.78% | 121.0 mg |
| Avicel PH101 (Microcrystalline cellulose) | Filler | 52.05% | 152 mg |
| Ac-Di-Sol (Croscarmellose sodium) | Disintegrant | 4.11% | 12 mg |
| Colloidal silicon dioxide | Glidant | 1.03% | 3 mg |
| Magnesium stearate | Lubricant | 1.03% | 3 mg |
| Hard gelatine capsule size 0 | Capsule shell | | 1 |

TABLE VIII

| Capsule B Composition (non ionic) | | | |
|---|---|---|---|
| Component | Function | Eq. 100 mg | Quantity per capsule |
| Compound 1 | Active ingredient | 41.78% | 121.0 mg |
| Avicel PH101 (Microcrystalline cellulose) | Filler | 52.05% | 152 mg |
| Kollidon CL (Crospovidone) | Disintegrant | 4.11% | 12 mg |
| Colloidal silicon dioxide | Glidant | 1.03% | 3 mg |
| Lubritab$^{RTM}$ | Lubricant | 1.03% | 3 mg |
| Hard gelatine capsule size 0 | Capsule shell | | 1 |

5.1.3. Results

When tested according to the protocol described above, as shown on FIG. 4 (Capsule A, ionic excipients) shows a continued degradation over the stability study period, characterised by the formation of an endotherm at around 221° C., which is not present on FIG. 5 (Capsule B, non-ionic excipients).

5.1.4. Tablets

5.1.4.1. Tablet Formation

Prior to blending, Compound 1.HCl.3H$_2$O is sieved (fractions 63-250 μm or <250 μm) and excipients are sieved (900 μm) using a stainless steel sieve. Compound 1.HCl.3H$_2$O and the excipients are then blended in a glass bottle using a Turbula Type T2A blender (Willy A. Bachofen, Switzerland) using the following procedure:
- Half of the filler is blended for 5 min
- Compound 1. HCl.3H$_2$O is added and blended for 20 min
- The second half of the filler, the disintegrant and the glidant are added and blended for 10 min
- The lubricant is added and blended for 5 min The tablets are the formed by compression on a single punch tablet press type XP1 (Korsch AG, Berlin, Germany). A 15 mm*8 2 mm oval shaped punch is used.

5.1.4.2. Tablet Hardness Determination

The tablet hardness or crushing strength is performed to determine tablet mechanical integrity or resistance to crushing. A Sotax H10 hardness tester is used (Sotax, Allschwil, Switzerland). Oblonged tablets are tested at their long side. A constant loading rate mode of 10 N/sec was applied. The apparatus also measures thickness and diameter/length of the tablet.

5.1.5. Tablet Disintegration

Disintegration testing is performed to determine whether tablets disintegrate within the prescribed time when placed in a liquid medium. A Sotax DT2 disintegration tester with automated end point detection was used (Sotax, Allschwil, Switzerland). The medium was purified water (Elix, Millipore) at a temperature of 37° C. The disintegration time is the time when all tested tablets have disintegrated.

5.1.6. Tablet Friability

Friability testing is performed to determine physical strength of uncoated tablets upon exposure to attrition. A Sotax FT2 friability tester equipped with a drum with an inside diameter of 287 mm and 38 mm was used (Sotax, Allschwil, Switzerland). The tablets are weighed and placed in the drum. The drum rotates 100 times at 25 rpm and the tablets are removed. Any loose dust or broken fragments from the tablets are removed. If no tablets are cracked, split or broken, they are weighed again and the friability is determined (percent of the lost mass with respect to the initial mass).

5.2. Stability Via In Vitro Dissolution Test

5.2.1. Overview

Tablets are kept in long term storage condition and accelerated conditions, and their dissolution rate is measured over 60 minutes at various time points from 0 to 12 months.

TABLE IX

| Stability conditions | |
|---|---|
| Model | Temp (° C.)/RH (%)/recipient |
| Cold conditions | 5° C./_/Closed recipient |
| Long term storage | 25° C./60% RH/Open recipient |
| Intermediate conditions | 30° C./65% RH/Open recipient |
| Accelerated conditions | 40° C./75% RH/Open recipient |

5.2.2. Protocol

The dissolution test is performed in an Evolution 6300 dissolution system (Distek, New Brunswick, N.J., USA), using the paddle method, combined with an Evolution 4300 automatic dissolution sampler (Distek, New Brunswick, N.J., USA). 0.01N HCl is used as dissolution medium. The temperature of the medium (900 mL) is kept at 37±0.5° C., while the rotational speed of the paddles is set at 75 rpm. Samples (filtered using Distek 45 μm filters) of 5 ml are withdrawn at 5, 10, 15, 20, 30, 45 and 60 min and analyzed by HPLC.

Samples are taken at T0, then every month up to 12 months, then at 18, 24 and 36 months; and each aliquots is then analysed by HPLC, Karl-Fisher titration, FT-IR, DSC, and XRPD.

The tablet composition is described below.

TABLE X

Tablet A Composition (Ionic excipient)

| Component | Function | | Eq. 100 mg Quantity per tablet |
|---|---|---|---|
| Compound 1 | Active ingredient | 24.40% | 122.0 mg |
| Avicel PH302 (Microcrystalline cellulose) | Filler | 72.85% | 364.25 mg |
| Ac-Di-Sol (Croscarmellose sodium) | Disintegrant | 2.00% | 10.00 mg |
| Colloidal silicon dioxide | Glidant | 0.25% | 1.25 mg |
| Magnesium stearate | Lubricant | 0.50% | 2.50 mg |
| Tablet weight | | | 500 mg |
| Tablet diameter | | | 15.1 mm |
| Tablet thickness | | | 5.3 mm |
| Compression | | | Korsch XP1 single punch press |
| Compression force | | | 5.0-5.5 kN |
| Ejection force | | | 290-340 N |

TABLE XI

Tablet B composition (Non- ionic excipient)

| Component | Function | | Eq. 100 mg Quantity per tablet |
|---|---|---|---|
| Compound 1 | Active ingredient | 24.20% | 121.0 mg |
| Avicel PH302 (Microcrystalline cellulose) | Filler | 71.55% | 357.75 mg |
| Kollidon CL (Crospovidone) | Disintegrant | 2.00% | 10.00 mg |
| Colloidal silicon dioxide | Glidant | 0.25% | 1.25 mg |
| Lubritab | Lubricant | 2.00% | 10.00 mg |
| Tablet weight | | | 500 mg |
| Tablet diameter | | | 15.1 mm |
| Tablet thickness | | | 5.4 mm |

TABLE XI-continued

Tablet B composition (Non- ionic excipient)

| Component | Function | Eq. 100 mg Quantity per tablet |
|---|---|---|
| Compression: | | Korsch XP1 single punch press |
| Compression force | | 4.9-5.6 kN |
| Ejection force | | 400-460 N |

5.2.3. Results

When subjected to this protocol, the dissolution rate is significantly lowered for Tablet A, as described in the tables below, in particular in accelerated stability conditions showing a severe drop in dissolution rate. In contrast, Tablet B dissolution is not affected in both long term storage conditions and accelerated stability conditions.

TABLE XII

Tablet A - Long term storage conditions
(Error! Reference source not found.)

| | | | | Time point | | | |
|---|---|---|---|---|---|---|---|
| Conditions | | 5 min | 10 min | 15 min | 20 min | 30 min | 45 min | 60 min |
| Initial | — | 86.7 | 94.4 | 95 | 95.5 | 95.5 | 95.7 | 95.4 |
| 1 Month | open | 91.8 | 98.8 | 100.2 | 100.2 | 100.5 | 100.4 | 99.8 |
| | closed | 91.6 | 98.3 | 99.3 | 99.7 | 99.5 | 99.8 | 99.8 |
| 2 Month | open | 89.4 | 95.8 | 96.5 | 96.7 | 96.5 | 97 | 96.6 |
| 3 Month | closed | 76.2 | 97.9 | 99.6 | 100.2 | 100.4 | 99.7 | 99.8 |
| | open | 90.5 | 96.9 | 98.8 | 99 | 98.9 | 98.5 | 98.3 |
| 6 Month | closed | 91.9 | 99.3 | 99.8 | 100.1 | 99.9 | 100.1 | 100 |
| | open | 76.7 | 94.4 | 95.7 | 96.1 | 96 | 95.9 | 95.9 |

TABLE XIII

Tablet A - Accelerated conditions
(Error! Reference source not found.)

| | | | | Time point | | | |
|---|---|---|---|---|---|---|---|
| Conditions | | 5 min | 10 min | 15 min | 20 min | 30 min | 45 min | 60 min |
| Initial | — | 86.7 | 94.4 | 95 | 95.5 | 95.5 | 95.7 | 95.4 |
| 1 Month | open | 84.6 | 93.3 | 95.7 | 96.7 | 97.8 | 98.5 | 99 |
| | closed | 87.9 | 98.5 | 99.5 | 99.9 | 100.2 | 100.4 | 100 |
| 2 Month | open | 79.8 | 86.3 | 90.7 | 92.4 | 94.2 | 95.6 | 96.3 |
| | closed | 83.7 | 92.7 | 95.8 | 96.6 | 97.5 | 98.2 | 98.4 |
| 3 Month | open | 65.4 | 84.3 | 90.6 | 93.5 | 94.9 | 95.9 | 97.5 |
| | closed | 77.4 | 90.1 | 92.7 | 94.2 | 95.3 | 95.4 | 96.3 |
| 6 Month | open | 34.8 | 60.9 | 75.7 | 82.8 | 88.6 | 92.4 | 93.8 |

TABLE XIV

Tablet B - Long term storage conditions
(Error! Reference source not found.)

| | | | | Time point (mn) | | | |
|---|---|---|---|---|---|---|---|
| Conditions | | 5 min | 10 min | 15 min | 20 min | 30 min | 45 min | 60 min |
| Initial | — | 91.3 | 97.2 | 98.2 | 98.9 | 98.6 | 98.7 | 98.6 |
| 1 Month | Open | 91.4 | 98.6 | 99.9 | 100.1 | 100.4 | 100.3 | 100.4 |
| | Closed | 93 | 99.2 | 100.4 | 100.6 | 100.4 | 100.5 | 100.5 |
| 2 Month | Open | 89.7 | 98.9 | 100.5 | 101 | 100.9 | 101.3 | 100.5 |
| | Closed | 89.4 | 98.2 | 99.1 | 100 | 100.3 | 99.8 | 98.9 |
| 3 Month | Open | 92.6 | 100.3 | 101.4 | 101 | 101.4 | 101.2 | 101 |
| 6 Month | Open | 88.7 | 97 | 98.3 | 98.6 | 98.6 | 98.7 | 99 |
| | Closed | 89.4 | 94 | 97.7 | 98.2 | 98.1 | 96.4 | 98.2 |

TABLE XV

Tablet B - Accelerated conditions (FIG. 9)

| | | | | Time point (mn) | | | |
|---|---|---|---|---|---|---|---|
| Conditions | | 5 min | 10 min | 15 min | 20 min | 30 min | 45 min | 60 min |
| Initial | — | 91.3 | 97.2 | 98.2 | 98.9 | 98.6 | 98.7 | 98.6 |
| 1 Month | Open | 88.7 | 95.3 | 97.1 | 97.8 | 97.8 | 98.2 | 98.5 |
| | Closed | 90.3 | 98.2 | 100.4 | 100.2 | 100.6 | 100.3 | 100.5 |
| 2 Month | Open | 88.4 | 95.6 | 98.2 | 98.7 | 99.3 | 99.5 | 99.5 |
| | Closed | 91.4 | 97.8 | 98.6 | 99.1 | 99.1 | 99 | 99.4 |
| 3 Month | Open | 89.5 | 100.7 | 101.9 | 101.5 | 102.1 | 101.2 | 101.7 |
| | Closed | 87.1 | 98 | 99.4 | 100.1 | 99.6 | 99.5 | 99.9 |
| 6 Month | Open | 85.5 | 95.7 | 96.4 | 97.4 | 98.1 | 98.3 | 98.1 |

5.2.4. DSC Stability

Tablet A and B are also monitored during the stability test via DSC thermogram (FIGS. 10-17).

As observed in the dissolution test, the DSC thermogram shows the formation of an endotherm at about 221° C., indicative of the formation of a new product and the instability of Compound 1.HCl.3H$_2$O formulated as tablet A. In contrast, this is not observed in the Formulation as Tablet B.

Conclusions

As demonstrated by the dissolution assay and the DSC thermogram analysis, in the presence of well-known commonly used ionic excipients, pharmaceutical composition comprising Compound 1.HCl.3H$_2$O undergo degradation. Surprisingly, this problem is solved in the pharmaceutical composition of the invention by the use of particular non-ionic excipients.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

Chemical names of compound as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Berishaj, M., Gao, S. P., Ahmed, S., Leslie, K., Al-Ahmadie, H., Gerald, W. L., Bornmann, W., Bromberg, J. F., 2007. Stat3 is tyrosine-phosphorylated through the interleukin-6/glycoprotein 130/Janus kinase pathway in breast cancer. Breast Cancer Res. BCR 9, R32. doi:10.1186/bcr1680

Constantinescu, S. N., Girardot, M., Pecquet, C., 2008. Mining for JAK—STAT mutations in cancer. Trends Biochem. Sci. 33, 122-131. doi:10.1016/j.tibs.2007.12.002

Dolgin, E., 2011. Companies hope for kinase inhibitor JAKpot. Nat. Rev. Drug Discov. 10, 717-718. doi:10.1038/nrd3571

European Medicine Agency, 2004. Clinical Investigation of Medicinal Products indicated for the Treatment of Psoriasis (No. CPMP/EWP/2454/02). London.

Ingersoll, K. S., Cohen, J., 2008. The impact of medication regimen factors on adherence to chronic treatment: a review of literature. J. Behav. Med. 31, 213-224. doi:10.1007/s10865-007-9147-y Kopf, M., Bachmann, M. F., Marsland, B. J., 2010. Averting inflammation by targeting the cytokine environment. Nat. Rev. Drug Discov. 9, 703-718. doi:10.1038/nrd2805

Menet, C. J. M., Smits, K. K., 2010. 5-Phenyl-[1,2,4]triazolo[1,5-A]pyridin-2-Yl Carboxamides as Jak Inhibitors. WO2010149769 (A1).

Mullighan, C. G., Zhang, J., Harvey, R. C., Collins-Underwood, J. R., Schulman, B. A., Phillips, L. A., Tasian, S. K., Loh, M. L., Su, X., Liu, W., Devidas, M., Atlas, S. R., Chen, I.-M., Clifford, R. J., Gerhard, D. S., Carroll, W. L., Reaman, G. H., Smith, M., Downing, J. R., Hunger, S. P., Willman, C. L., 2009. JAK mutations in high-risk childhood acute lymphoblastic leukemia. Proc. Natl. Acad. Sci. U.S.A. 106, 9414-9418. doi:10.1073/pnas.0811761106

Naka, T., Nishimoto, N., Kishimoto, T., 2002. The paradigm of IL-6: from basic science to medicine. Arthritis Res. 4, S233-S242. doi:10.1186/ar565

O'Dell, J. R., 2004. Therapeutic Strategies for Rheumatoid Arthritis. N. Engl. J. Med. 350, 2591-2602. doi:10.1056/NEJMra040226

O'Sullivan, L. A., Liongue, C., Lewis, R. S., Stephenson, S. E. M., Ward, A. C., 2007. Cytokine receptor signaling through the Jak-Stat-Socs pathway in disease. Mol. Immunol 44, 2497-2506. doi:10.1016/j.molimm.2006.11.025

Punwani, N., Scherle, P., Flores, R., Shi, J., Liang, J., Yeleswaram, S., Levy, R., Williams, W., Gottlieb, A., 2012. Preliminary clinical activity of a topical JAK½ inhibitor in the treatment of psoriasis. J. Am. Acad. Dermatol. 67, 658-664. doi:10.1016/j.jaad.2011.12.018

Rowe, R. C., Sheskey, P. J., Quinn, M. E., 2009. Handbook of Pharmaceutical Excipients, Sixth Edition, 6th ed. Pharmaceutical Press, London.

Smolen, J. S., Steiner, G., 2003. Therapeutic strategies for rheumatoid arthritis. Nat. Rev. Drug Discov. 2, 473-488. doi:10.1038/nrd1109

Tam, L., McGlynn, L. M., Traynor, P., Mukherjee, R., Bartlett, J. M. S., Edwards, J., 2007. Expression levels of the JAK/STAT pathway in the transition from hormone-sensitive to hormone-refractory prostate cancer. Br. J. Cancer 97, 378-383. doi:10.1038/sj.bjc.6603871

Vainchenker, W., Dusa, A., Constantinescu, S. N., 2008. JAKs in pathology: Role of Janus kinases in hematopoietic malignancies and immunodeficiencies. Semin. Cell Dev. Biol. 19, 385-393. doi:10.1016/j.semcdb.2008.07.002

Verstovsek, S., 2009. Therapeutic potential of JAK2 inhibitors. ASH Educ. Program Book 2009, 636-642. doi:10.1182/asheducation-2009.1.636

Xiang, Z., Zhao, Y., Mitaksov, V., Fremont, D. H., Kasai, Y., Molitoris, A., Ries, R. E., Miner, T. L., McLellan, M. D., DiPersio, J. F., Link, D. C., Payton, J. E., Graubert, T. A., Watson, M., Shannon, W., Heath, S. E., Nagarajan, R., Mardis, E. R., Wilson, R. K., Ley, T. J., Tomasson, M. H., 2008. Identification of somatic JAK1 mutations in patients with acute myeloid leukemia. Blood 111, 4809-4812. doi:10.1182/blood-2007-05-090308

Zenz, R., Eferl, R., Kenner, L., Florin, L., Hummerich, L., Mehic, D., Scheuch, H., Angel, P., Tschachler, E., Wagner, E. F., 2005. Psoriasis-like skin disease and arthritis caused by inducible epidermal deletion of Jun proteins. Nature 437, 369-375. doi:10.1038/nature03963

Zhang, Q., Nowak, I., Vonderheid, E. C., Rook, A. H., Kadin, M. E., Nowell, P. C., Shaw, L. M., Wasik, M. A., 1996. Activation of Jak/STAT proteins involved in signal transduction pathway mediated by receptor for interleukin 2 in malignant T lymphocytes derived from cutaneous anaplastic large T-cell lymphoma and Sezary syndrome. Proc. Natl. Acad. Sci. U.S.A. 93, 9148-9153.

Zikherman, J., Weiss, A., 2011. Unraveling the functional implications of GWAS: how T cell protein tyrosine phosphatase drives autoimmune disease. J. Clin. Invest. 121, 4618-4621. doi:10.1172/JCI60001

The invention claimed is:

1. A pharmaceutical composition comprising:
(i) 1-50% by weight of a 1:1:3 [Compound 1:HCl:H$_2$O] adduct of Compound 1:

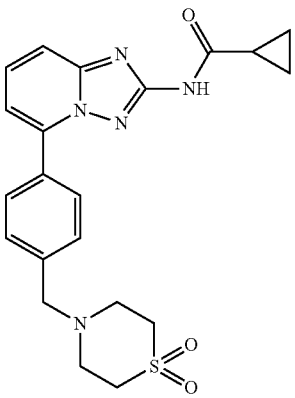

(ii) 49.9-94% by weight of an inert solid diluent; and
(iii) 0.1-5% by weight of a lubricant.

2. The pharmaceutical composition according to claim 1, wherein the inert solid diluent is selected from cellulose powdered, silicified microcrystalline cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, and xylitol.

3. The pharmaceutical composition according to claim 1, wherein the inert solid diluent is microcrystalline cellulose.

4. The pharmaceutical composition according to claim 1, wherein the lubricant is non-ionic.

5. The pharmaceutical composition according to claim 1, wherein the lubricant is selected from canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, and hydrogenated vegetable oil.

6. The pharmaceutical composition according to claim 1, wherein the lubricant is a vegetable oil, glycerol dibehenate, or polyethylene glycol 10,000.

7. The pharmaceutical composition according to claim 1, wherein the pharmaceutical composition further comprises a non-ionic disintegrant constituting from 0.1 to 5% by weight of the pharmaceutical composition.

8. The pharmaceutical composition according to claim 7, wherein the disintegrant is selected from alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, and povidone.

9. The pharmaceutical composition according to claim 7, wherein the disintegrant is polyvinylpolypyrrolidone, pregelatinised starch, or microcrystalline cellulose.

10. The pharmaceutical composition according to claim 1, wherein the pharmaceutical composition further comprises a glidant constituting from 0.1 to 0.5% by weight of the pharmaceutical composition.

11. The pharmaceutical composition according to claim 10, wherein the glidant is selected from powdered cellulose, colloidal silicon dioxide, hydrophobic colloidal silica, silicon dioxide, and talc.

12. The pharmaceutical composition according to claim 1, wherein the 1:1:3 [Compound 1:HCl:$H_2O$] adduct of Compound 1 is characterized at least by a powder X-ray diffraction peak in all of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, and 32.7° 2θ±0.2° 2θ.

13. The pharmaceutical composition according to claim 1, wherein at least 90% of said composition is dissolved within about 5 minutes after storage for 1 month in an open recipient at 40° C. I 75% relative humidity, as measured using the paddle method at a speed of 75 rpm at 37±0.5° C. in 0.01 N HCl as dissolution medium.

14. The pharmaceutical composition according to claim 1, comprising a further therapeutic agent.

15. The pharmaceutical composition according to claim 14, wherein the further therapeutic agent is an agent for the prophylaxis and/or treatment of rheumatoid arthritis.

16. The pharmaceutical composition according to claim 1, which is in a tablet form.

17. The pharmaceutical composition according to claim 1, which is in a capsule form.

18. A method for the prophylaxis and/or treatment of rheumatoid arthritis, said method comprising administering an amount of a pharmaceutical composition according to claim 1 sufficient to effect said prophylaxis and/or treatment.

* * * * *